(12) United States Patent
Lemurell et al.

(10) Patent No.: US 7,842,684 B2
(45) Date of Patent: Nov. 30, 2010

(54) DIPHENYLAZETIDINONE DERIVATIVES POSSESSING CHOLESTEROL ABSORPTION INHIBITOR ACTIVITY

(75) Inventors: Malin Lemurell, Molndal (SE); Ingemar Starke, Molndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/298,543

(22) PCT Filed: Apr. 25, 2007

(86) PCT No.: PCT/SE2007/000400
§ 371 (c)(1), (2), (4) Date: Oct. 27, 2008

(87) PCT Pub. No.: WO2007/126358
PCT Pub. Date: Nov. 8, 2007

(65) Prior Publication Data
US 2009/0069285 A1 Mar. 12, 2009

Related U.S. Application Data

(60) Provisional application No. 60/795,461, filed on Apr. 27, 2006.

(51) Int. Cl.
C07D 205/08 (2006.01)
A61K 31/397 (2006.01)
A61P 31/06 (2006.01)
A61P 9/10 (2006.01)
A61P 25/28 (2006.01)

(52) U.S. Cl. .................. 514/210.02; 540/360; 560/35; 562/507; 562/561

(58) Field of Classification Search ............... 540/360; 514/210.02
See application file for complete search history.

(56) References Cited

U.S. PATENT DOCUMENTS

| | | | |
|---|---|---|---|
| 5,360,817 A | 11/1994 | Von Izstein et al. |
| 5,631,365 A | 5/1997 | Rosenblum et al. |
| 5,661,145 A | 8/1997 | Davis |
| 5,739,321 A | 4/1998 | Wu et al. |
| 5,756,470 A | 5/1998 | Yumibe et al. |
| 5,767,115 A | 6/1998 | Rosenblum et al. |
| 5,846,966 A | 12/1998 | Rosenblum et al. |
| 5,886,171 A | 3/1999 | Wu et al. |

(Continued)

FOREIGN PATENT DOCUMENTS

| | | |
|---|---|---|
| EP | 524595 | 1/1993 |
| EP | 1362855 | 11/2003 |
| EP | 1413331 | 4/2004 |
| WO | 9302048 | 2/1993 |
| WO | 9414433 | 7/1994 |
| WO | 9417038 | 8/1994 |
| WO | 9501961 | 1/1995 |
| WO | 9508532 | 3/1995 |
| WO | 9526334 | 10/1995 |
| WO | 9535277 | 12/1995 |
| WO | 9609827 | 4/1996 |
| WO | 9616037 | 5/1996 |
| WO | 9619450 | 6/1996 |

(Continued)

OTHER PUBLICATIONS

Zaks et al., "Enzymatic glucuronidation of a novel cholesterol absorption inhibitor," Appl Biochem Biotechnol. (1998) 73 (2-3):205-214.

(Continued)

*Primary Examiner*—Mark L Berch
(74) *Attorney, Agent, or Firm*—Pepper Hamilton LLP

(57) ABSTRACT

The present invention provides 2-azetidinone derivatives, or pharmaceutically acceptable salts, solvates, solvates of such salts and prodrugs thereof, comprising formula (I):

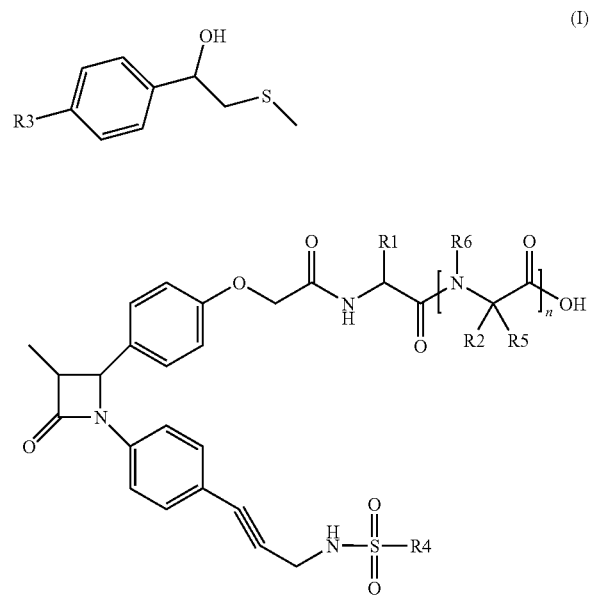

wherein the substituents are as herein defined. The compounds possess cholesterol absorption inhibitory activity and are accordingly of value in the treatment of disease states associated with hyperlipidaemic conditions.

12 Claims, No Drawings

U.S. PATENT DOCUMENTS

| | | | |
|---|---|---|---|
| 5,919,672 | A | 7/1999 | Homann et al. |
| RE37,721 | E | 5/2002 | Rosenblum et al. |
| 7,470,678 | B2 * | 12/2008 | Starke et al. .......... 514/210.09 |
| 2003/0119428 | A1 | 6/2003 | Davis et al. |
| 2003/0119757 | A1 | 6/2003 | Davis |
| 2004/0018060 | A1 | 1/2004 | Knezek |
| 2004/0018061 | A1 | 1/2004 | Jansson |
| 2004/0254369 | A1 | 12/2004 | Framroze |
| 2005/0096307 | A1 | 5/2005 | Graziano |
| 2005/0267049 | A1 | 12/2005 | Goulet et al. |
| 2006/0046996 | A1 | 3/2006 | Aoki et al. |
| 2006/0069080 | A1 | 3/2006 | Veltri |
| 2007/0049748 | A1 | 3/2007 | Uppala et al. |
| 2007/0078098 | A1 | 4/2007 | DeVita et al. |
| 2007/0129540 | A1 | 6/2007 | Framroze |
| 2008/0064676 | A1 * | 3/2008 | Alenfalk et al. ........ 514/210.02 |
| 2008/0070890 | A1 * | 3/2008 | Burnett et al. ......... 514/210.05 |
| 2010/0048529 | A1 * | 2/2010 | Dahlstrom et al. ..... 514/210.02 |
| 2010/0048530 | A1 * | 2/2010 | Dahlstrom et al. ..... 514/210.15 |
| 2010/0099657 | A2 * | 4/2010 | Alenfalk et al. ........ 514/210.02 |
| 2010/0125059 | A1 * | 5/2010 | Nakano et al. ......... 514/210.02 |
| 2010/0137273 | A1 * | 6/2010 | Alenfalk et al. ........ 514/210.02 |
| 2010/0152156 | A1 * | 6/2010 | Dahlstrom et al. ..... 514/210.02 |
| 2010/0168075 | A1 * | 7/2010 | Dahlstrom et al. ..... 514/210.02 |

FOREIGN PATENT DOCUMENTS

| | | |
|---|---|---|
| WO | 9716424 | 5/1997 |
| WO | 9716455 | 5/1997 |
| WO | 9745406 | 12/1997 |
| WO | 0020623 | 4/2000 |
| WO | 0034240 | 6/2000 |
| WO | 0038725 | 7/2000 |
| WO | 0060107 | 10/2000 |
| WO | 0063703 | 10/2000 |
| WO | 0218432 | 3/2002 |
| WO | 0250027 | 6/2002 |
| WO | 0250060 | 6/2002 |
| WO | 0250068 | 6/2002 |
| WO | 0250090 | 6/2002 |
| WO | 02058685 | 8/2002 |
| WO | 02058696 | 8/2002 |
| WO | 02058731 | 8/2002 |
| WO | 02058732 | 8/2002 |
| WO | 02058733 | 8/2002 |
| WO | 02058734 | 8/2002 |
| WO | 02066464 | 8/2002 |
| WO | 02072104 | 9/2002 |
| WO | 02079174 | 10/2002 |
| WO | 02096415 | 12/2002 |
| WO | 03026643 | 4/2003 |
| WO | 03026644 | 4/2003 |
| WO | 03088962 | 10/2003 |
| WO | 04000803 | 12/2003 |
| WO | 04000804 | 12/2003 |
| WO | 04000805 | 12/2003 |
| WO | 2004005247 | 1/2004 |
| WO | 2004009913 | 1/2004 |
| WO | 2004010948 | 2/2004 |
| WO | 2004010993 | 2/2004 |
| WO | 2004014947 | 2/2004 |
| WO | 2004043456 | 5/2004 |
| WO | 2004043457 | 5/2004 |
| WO | 2004081002 | 9/2004 |
| WO | 2004107958 | 12/2004 |
| WO | 2005000353 | 1/2005 |
| WO | 2005021495 | 3/2005 |
| WO | 2005021497 | 3/2005 |
| WO | 2005033100 | 4/2005 |
| WO | 2005042692 | 5/2005 |
| WO | 2005044256 | 5/2005 |
| WO | 2005047248 | 5/2005 |
| WO | 2005049592 | 6/2005 |
| WO | 2005058316 | 6/2005 |
| WO | 2005061451 | 7/2005 |
| WO | 2005061452 | 7/2005 |
| WO | 2005062824 | 7/2005 |
| WO | 2005062897 | 7/2005 |
| WO | 2005066120 | 7/2005 |
| WO | 2005067903 | 7/2005 |
| WO | 2005069900 | 8/2005 |
| WO | 2005113495 | 12/2005 |
| WO | 2005113496 | 12/2005 |
| WO | 2006017257 | 2/2006 |
| WO | 2006060808 | 6/2006 |
| WO | 2006068990 | 6/2006 |
| WO | 2006072957 | 7/2006 |
| WO | 2006086562 | 8/2006 |
| WO | 2006102674 | 9/2006 |
| WO | 2006107936 | 10/2006 |
| WO | 2006116499 | 11/2006 |
| WO | 2006121861 | 11/2006 |
| WO | 2006122186 | 11/2006 |
| WO | 2006122216 | 11/2006 |
| WO | 2006124713 | 11/2006 |
| WO | 2006127893 | 11/2006 |
| WO | 2006134604 | 12/2006 |
| WO | 2006137080 | 12/2006 |
| WO | 2006137782 | 12/2006 |
| WO | 2006137792 | 12/2006 |
| WO | 2006137793 | 12/2006 |
| WO | 2006137794 | 12/2006 |
| WO | 2006137795 | 12/2006 |
| WO | 2006137796 | 12/2006 |
| WO | 2006137797 | 12/2006 |
| WO | 2006138163 | 12/2006 |
| WO | 2007003365 | 1/2007 |
| WO | 2007008529 | 1/2007 |
| WO | 2007008541 | 1/2007 |
| WO | 2007015161 | 2/2007 |
| WO | 2007016643 | 2/2007 |
| WO | 2007017705 | 2/2007 |
| WO | 2007030721 | 3/2007 |
| WO | 2007058335 | 5/2007 |
| WO | 2007059871 | 5/2007 |
| WO | 2007072088 | 6/2007 |
| WO | 2007075702 | 7/2007 |

OTHER PUBLICATIONS

Groning et al., "Dosage forms with controlled gastrointestinal passage—studies on the absorption of nitrofurantoin," Int J. Pharm (1989) 56:111-116.

Journal of the American College of Cardiology (2000) 35(1):252A.

Van Heek et al., "Comparison of the activity and disposition of the novel cholesterol absorption inhibitor, SCH58235, and its glucuronide, SCH60663," Br. J. Pharmacol (2000) 129(8):1748-1754.

Wu et al., "A Novel One-Step Diastereo- and Enantioselective Formation of trans-Azetidinones and Its Application to the Total Synthesis of Cholesterol Absorption Inhibitors," J. Org. Chem (1999) 64:3714-3718.

Vaccaro et al., "Carboxy-substituted 2-azetidinones as cholesterol absorption inhibitors," Bioorganic & Medicinal Chemistry Letters (1998) 8:319-322.

Rosenblum et al., "Discovery of 1-(4-fluorophenyl)-(3R)-[3-(4-fluorophenyl)-(3S)-hydroxypropyl]-(4S)-(4-hydroxyphenyl)-2-azetidinone (SCH 58235): a designed, potent, orally active inhibitor of cholesterol absorption.," J. Med Chem (1998) 41:973-980.

Burnett et al., "2-Azetidinones as Inhibitors of Cholesterol Absorption," Journal of Medicinal Chemistry (1994) 37 (12):1733-1736.

Sobieszczyk et al., "Acute pulmonary embolism: don't ignore the platelet," Circulation (2002) 106(14):1748-1749.

Castaner et al., "Ezetimibe Hypolipidemic, Cholesterol absorption inhibitor," Drugs of the Future (2000) 25(7):679-685.

Vaccaro et al., "Sugar-substituted 2-azetidinone cholesterol absorption inhibitors: Enhanced potency by modification of the sugar," Bioorganic & Medicinal Chemistry Letters (1998) 8:313-318.

Kirkup et al., "(í)-SCH 57939: synthesis and pharmacological properties of a potent, metabolically stable cholesterol absorption inhibitor," Bioorganic & Medicinal Chemistry Letters (1996) 6(17):2069-2072.

Fu et al., "Process for preparing Ezetimibe intermediate by an acid enhanced chemo- and enantioselective CBS catalyzed ketone reduction," Tetrahedron Letters (2003) 44:801-804.

Mounsey et al., "Diet may slow progression of diabetic nephropathy," The Journal of Family Practice (2003) 52 (9):672-673.

Burnett et al., "2-Azetidinones as Inhibitors of Cholesterol Absorption," J. Med Chem (1994) 12:1733-1736.

McKittrick et al., Stereoselective synthesis and biological activity of cis azetidinones as cholesterol absorption inhibitors, Bioorganic & Medicinal Chemistry Letters (1996) 6(16):1947-1950.

Clader et al., "2-Azetidinone Cholesterol Absorption Inhibitors: Structure-Activity Relationships on the Heterocyclic Nucleus," J. Med Chem (1996) 39:3684-3693.

Clader "The discovery of ezetimibe: a view from outside the receptor," J Med Chem (2004) 47(1):1-9.

Yang et al., "Allelic Variants in Long-QT Disease Genes in Patients With Drug-Associated Torsades de Pointes,"Circulation (2002) 105(16):1943-1948.

Maughan et al., "Gastric emptying and fluid availability after ingestion of glucose and soy protein hydrolysate solutions in man," G.E. Exp. Physiol (2004) 89:101-108.

Vist et al., "The effect of osmolality and carbohydrate content on the rate of gastric emptying of liquids in man," Physiol (London) (1995) 486:523-531.

Elias et al., "The slowing of gastric emptying by monosaccharides and disaccharides in test meals," Physiol (London) (1968) 194:317-326.

Hunt "Does calcium mediate slowing of gastric emptying by fat in humans?," Am J Physiol (1983) 244:G89-G94.

Hunt et al., "A relation between the chain length of fatty acids and the slowing of gastric emptying," J. Physiol (London) (1968) 194:324-336.

Fisher et al., "Effects of Hydrochlorides of Amino Acids in Test Meals on Gastric Emptying," Digestion (1977) 16:18-22.

Burn-Murdock et al., "The slowing of gastric emptying by proteins in test meals," J Physiol (London) (1978).

Groning et al., "Oral dosage forms with comtrolled gastrointestinal transit," Drug Dev.Ind. Pharm (1984) 10:527-539.

* cited by examiner

DIPHENYLAZETIDINONE DERIVATIVES POSSESSING CHOLESTEROL ABSORPTION INHIBITOR ACTIVITY

CROSS-REFERENCE TO RELATED APPLICATIONS

This application is the U.S. National Stage filing of International Application Serial No. PCT/SE2007/000400 filed Apr. 25, 2007, which claims priority to U.S. Provisional Application Ser. No. 60/795,461 filed Apr. 27, 2006, each of which is incorporated herein by reference in its entirety.

This invention relates to 2-azetidinone derivatives, or pharmaceutically acceptable salts, solvates, solvates of such salts and prodrugs thereof. These 2-azetidinones possess cholesterol absorption inhibitory activity and are accordingly of value in the treatment of disease states associated with hyperlipidaemic conditions. They are therefore useful in methods of treatment of a warm-blooded animal, such as man. The invention also relates to processes for the manufacture of said 2-azetidinone derivatives, to pharmaceutical compositions containing them and to their use in the manufacture of medicaments to inhibit cholesterol absorption in a warm-blooded animal, such as man. A further aspect of this invention relates to the use of the compounds of the invention in the treatment of dyslipidemic conditions.

Atherosclerotic coronary artery disease is a major cause of death and morbidity in the western world as well as a significant drain on healthcare resources. It is well-known that hyperlipidaemic conditions associated with elevated concentrations of total cholesterol and low density lipoprotein (LDL) cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930-1938 and "Diabetes and Cardiovascular Disease: A Statement for Healthcare Professionals from the American Heart Association" Grundy S, Benjamin I., Burke G., et al; Circulation, 1999, 100, 1134-46).

The concentration of plasma cholesterol depends on the integrated balance of endogenous and exogenous pathways of cholesterol metabolism. In the endogenous pathway, cholesterol is synthesized by the liver and extra hepatic tissues and enters the circulation as lipoproteins or is secreted into bile. In the exogenous pathway cholesterol from dietary and biliary sources is absorbed in the intestine and enters the circulation as component of chylomicrons. Alteration of either pathway will affect the plasma concentration of cholesterol.

The precise mechanism by which cholesterol is absorbed from the intestine is however not clear. The original hypothesis has been that cholesterol is crossing the intestine by unspecific diffusion. But more recent studies are suggesting that there are specific transporters involved in the intestinal cholesterol absorption. (See for instance New molecular targets for cholesterol-lowering therapy Izzat, N. N., Deshazer, M. E. and Loose-Mitchell D. S. JPET 293:315-320, 2000.)

A clear association between reduction of total cholesterol and (LDL) cholesterol and decreased instance of coronary artery disease has been established, and several classes of pharmaceutical agents are used to control serum cholesterol. There major options to regulate plasma cholesterol include (i) blocking the synthesis of cholesterol by agents such as HMG-CoA reductase inhibitors, for example statins such as simvastatin and fluvastatin, which also by up-regulation of LDL-receptors will promote the cholesterol removal from the plasma; (ii) blocking the bile acid reabsorption by specific agents resulting in increased bile acid excretion and synthesis of bile acids from cholesterol with agents such as bile acid binders, such as resins e.g. cholestyramine and cholestipol; and (iii) by blocking the intestinal uptake of cholesterol by selective cholesterol absorption inhibitors. High density lipoprotein (HDL) elevating agents such as fibrates and nicotinic acid analogues have also been employed.

Even with the current diverse range of therapeutic agents, a significant proportion of the hypercholesterolaemic population is unable to reach target cholesterol levels, or drug interactions or drug safety preclude the long term use needed to reach the target levels. Therefore there is still a need to develop additional agents that are more efficacious and are better tolerated.

Compounds possessing such cholesterol absorption inhibitory activity have been described, see for instance the compounds described in WO 93/02048, WO 94/17038, WO 95/08532, WO 95/26334, WO 95/35277, WO 96/16037, WO 96/19450, WO 97/16455, WO 02/50027, WO 02/50060, WO 02/50068, WO 02/50090, WO 02/66464, WO 04/000803, WO 04/000804, WO04/000805, WO04/01993, WO04/010948, WO04/043456 WO 04/043457, WO 04/081002, WO05/000353, WO05/021495, WO05/021497, WO05/033100, WO05044256, WO05044248, WO 05/062824, WO05061451, WO05061452, U.S. Pat. No. 5,756,470, U.S. Pat. No. 5,767,115, US 20040180860, US20040180861, US20050267049 and U.S. RE37721.

The present invention is based on the discovery that certain 2-azetidinone derivatives surprisingly inhibit cholesterol absorption. Such properties are expected to be of value in the treatment of disease states associated with hyperlipidaemic conditions. The compounds of the present invention are not disclosed in any of the above applications and we have surprisingly found that the compounds of the present invention possess beneficial efficacious, metabolic and toxicological profiles that make them particularly suitable for in vivo administration to a warm blooded animal, such as man. In particular certain compounds of the present invention have a low degree of absorption whilst retaining their ability to inhibit cholesterol absorption.

Accordingly there is provided a compound of formula (I):

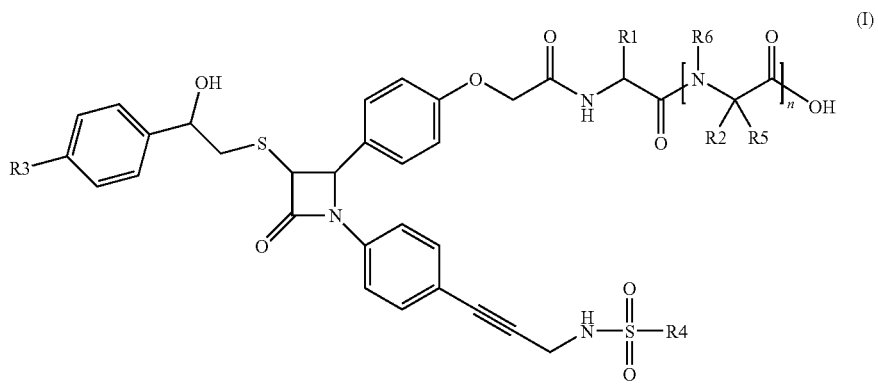

wherein:
$R^1$ is hydrogen, $C_{1-6}$alkyl, $C_{3-6}$cycloalkyl or aryl;
$R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, $(C_1-C_4)_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl, $C_{1-6}$alkoxy, or cyano;
$R^3$ is hydrogen, alkyl, halo, $C_{1-6}$alkoxy or $C_{1-6}$ alkylS-;
$R^4$ is methyl or aryl;
$R^6$ is hydrogen, $C_{1-6}$ alkyl, or aryl$C_{1-6}$ alkyl;
wherein $R^5$ and $R^2$ may form a ring with 2-7 carbon atoms and wherein $R^6$ and $R^2$ may form a ring with 3-6 carbon atoms; n=0 or 1;

or a pharmaceutically acceptable salt, solvate, solvate of such a salt or a prodrug thereof.

In one aspect of the invention it is provided for a compound of formula (I2):

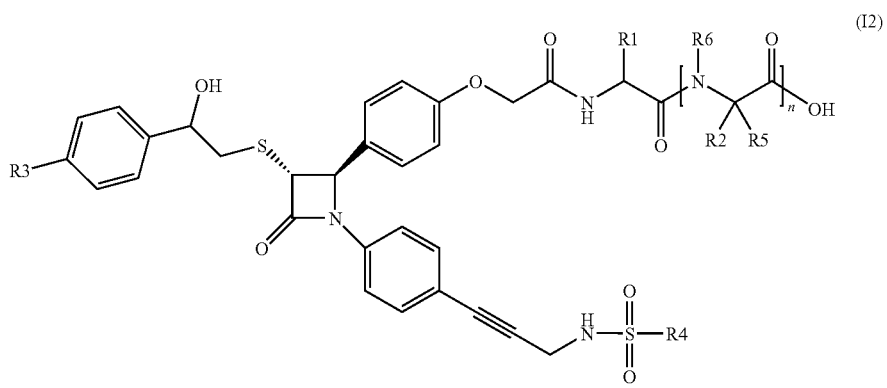

wherein:
$R^1$ is hydrogen, $C_{1-6}$alkyl, $C_{3-6}$cycloalkyl or aryl; $R^2$ and $R^5$ are independently hydrogen, a branched or unbranched $C_{1-6}$alkyl, hydroxy, amino, guanidino, cyano, carbamoyl, carboxy, $C_{1-6}$alkoxy, aryl $C_{1-6}$alkoxy, $(C_1-C_4)_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl, $C_{1-6}$alkoxy, or cyano;
$R^3$ is hydrogen, alkyl, halo, $C_{1-6}$alkoxy or $C_{1-6}$ alkylS-;
$R^4$ is methyl or aryl;
$R^6$ is hydrogen, $C_{1-6}$ alkyl, or aryl$C_{1-6}$ alkyl;
wherein $R^5$ and $R^2$ may form a ring with 2-7 carbon atoms and wherein $R^6$ and $R^2$ may form a ring with 3-6 carbon atoms; n=0 or 1 or a pharmaceutically acceptable salt, solvate, solvate of such a salt or a prodrug thereof.
(I2)

wherein variable groups are defined above as for formula (I). What is said further for formula (I) will, apart from the process schemes below, apply also to formula (I2).

According to one aspect of the invention $R^1$ is hydrogen. According to one aspect of the invention, $R^2$ and $R^5$ are hydrogen or a branched or unbranched $C_{1-6}$alkyl, $C_{3-6}$cycloalkyl or aryl; wherein said $C_{1-6}$alkyl may be optionally substituted by one or more hydroxyl or amino. According to one aspect of the invention, $R^3$ is halo. According to one aspect of the invention, $R^3$ is fluorine. According to one aspect of the invention, $R^6$ is hydrogen. According to one aspect of the invention, $R^1$ is hydrogen; $R^2$ and $R^5$ are hydrogen or a branched or unbranched $C_{1-6}$alkyl, $C_{3-6}$cycloalkyl or aryl; wherein said $C_{1-6}$alkyl may be optionally substituted by one or more hydroxyl or amino and $R^3$ and $R^6$ are halo.

According to an aspect of the invention, a compound according to the invention is chosen from one of the following compounds:

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-3-cyclohexyl-D-alanine;

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-D-valine;

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-3-methyl-D-valine;

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-D-lysine;

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycylglycine; and N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycine.

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include propyl, isopropyl and t-butyl. However, references to individual alkyl groups such as 'propyl' are specific for the straight-chained version only and references to individual branched chain alkyl groups such as 'isopropyl' are specific for the branched chain version only. A similar convention applies to other radicals, for example "phenyl$C_{1-6}$alkyl" would include benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"$C_{3-6}$cycloalkyl" refers to cyclopropyl, cyclobutyl, cyclopentyl and cyclohexyl.

A suitable pharmaceutically acceptable salt of a compound of the invention, or other compounds disclosed herein, is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I), or other compounds disclosed herein, may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I), or other compounds disclosed herein, containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I), or other compounds disclosed herein, containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I), or other compounds disclosed herein, containing a carboxy group is, for example, a N-$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess cholesterol absorption inhibitory activity.

The invention relates to any and all tautomeric forms of the compounds of the formula (I) that possess cholesterol absorption inhibitory activity.

It is also to be understood that certain compounds of the formula (I) can exist in solvated as well as unsolvated forms such as, for example, hydrated forms. It is to be understood that the invention encompasses all such solvated forms which possess cholesterol absorption inhibitory activity.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a pro-drug thereof which process (wherein variable groups are, unless otherwise specified, as defined in formula (I)) comprises of:

Another aspect of the present invention provides a process for preparing a compound of formula (I2) or a pharmaceutically acceptable salt, solvate, solvate of such a salt or a pro-drug thereof which process (wherein variable groups are, unless otherwise specified, as defined in formula (I)) comprises of:

Process 1) Reacting a Compound of Formula (II):

(II)

with a compound of formula (III):

(III)

wherein L is a displaceable group;

Process 2) Reacting an Acid of Formula (IV):

(IV)

or an activated derivative thereof; with an amine of formula (V):

(V)

Process 3): Reacting an Acid of Formula (VI):

(VI)

or an activated derivative thereof, with an amine of formula (VII):

(VII)

Process 4): Reducing a Compound of Formula (VIII):
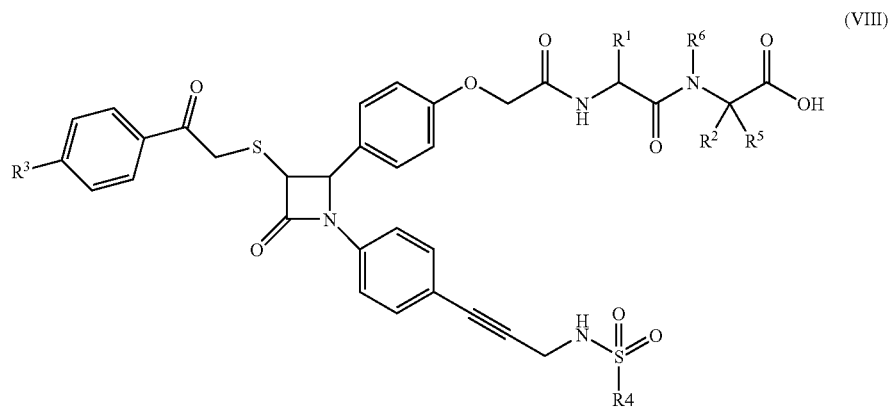
Process 5): Reacting a Compound of Formula (IX):
Process 6): Reacting a Compound of Formula (XI):
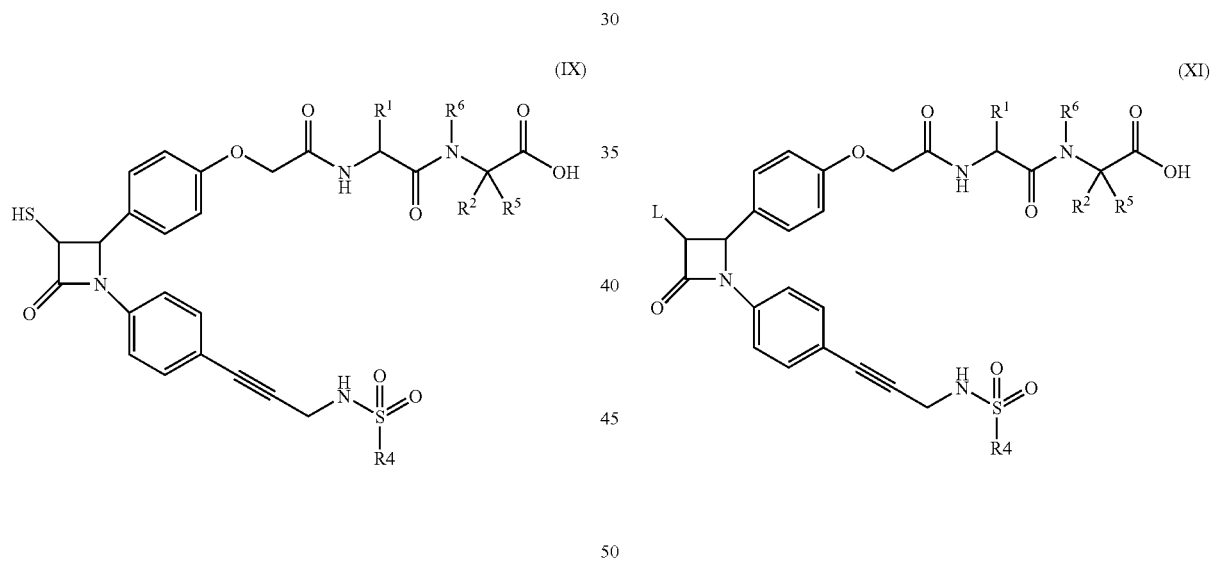
with a compound of formula (X):
wherein L is a displaceable group; with a compound of formula (XII):
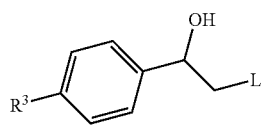
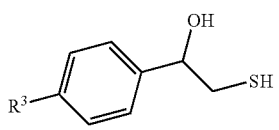
wherein L is a displaceable group;

Process 7): De-Esterifying a Compound of Formula (XIII)

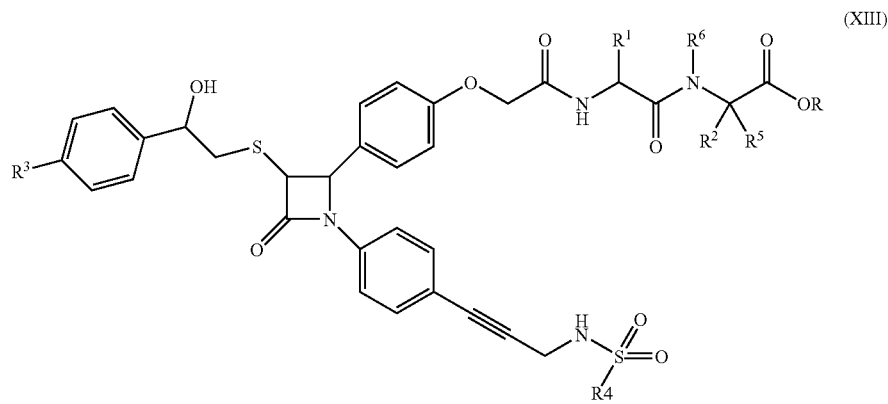

wherein the group C(O)OR is an ester group;

and thereafter if necessary or desirable:

i) converting a compound of the formula (I) into another compound of the formula (I);
ii) removing any protecting groups;
iii) forming a pharmaceutically acceptable salt, solvate, solvate of such a salt or a prodrug; or
iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1, WO05062824 and WO 05061452. Alternatively they can be prepared by the following reactions.

Process 1): Alcohols of formula (II) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Another aspect of the present invention provides a process for preparing a compound of formula (I2) or a pharmaceutically acceptable salt, solvate, solvate of such a salt or a prodrug thereof which process (wherein variable groups are, unless otherwise specified, as defined in formula (I)) comprises of:

Process 1) Reacting a Compound of Formula (II2):

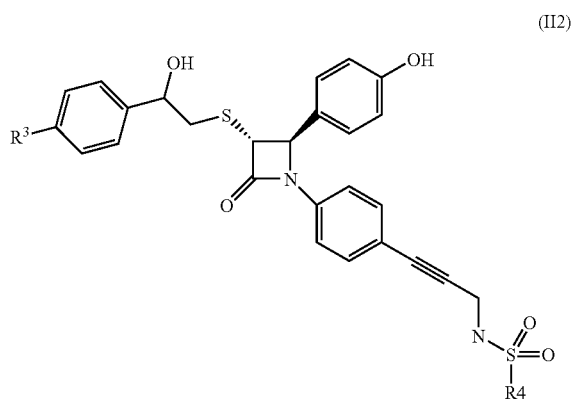

with a compound of formula (III):

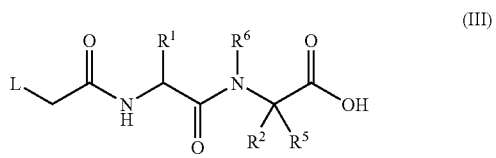

wherein L is a displaceable group;

Process 2) Reacting an Acid of Formula (IV2):
Process 3): Reacting an Acid of Formula (VI2):
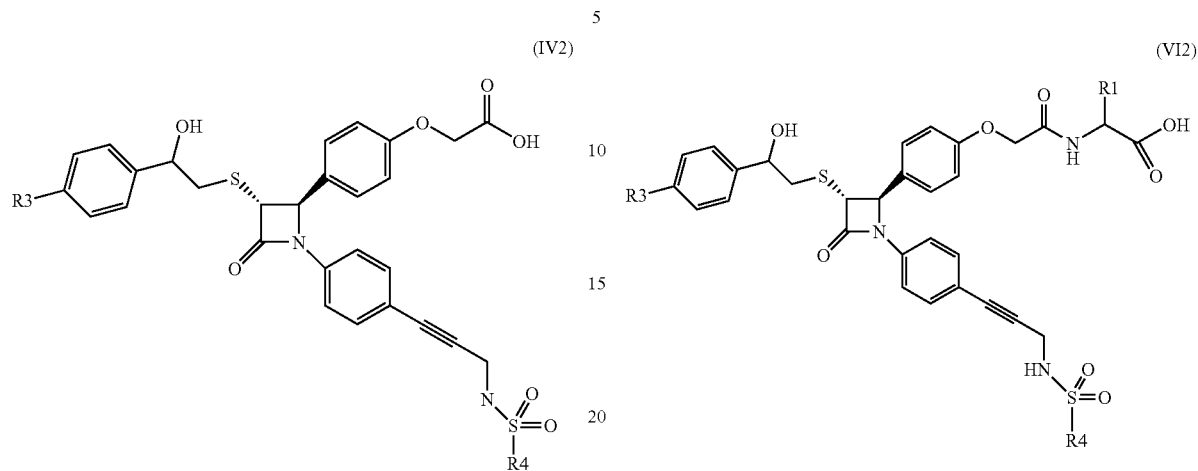
or an activated derivative thereof; with an amine of formula (V):
or an activated derivative thereof, with an amine of formula (VII):
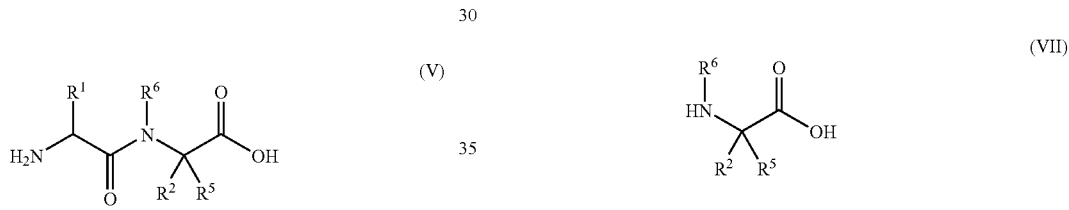
Process 4): Reducing a Compound of Formula (VIII2):
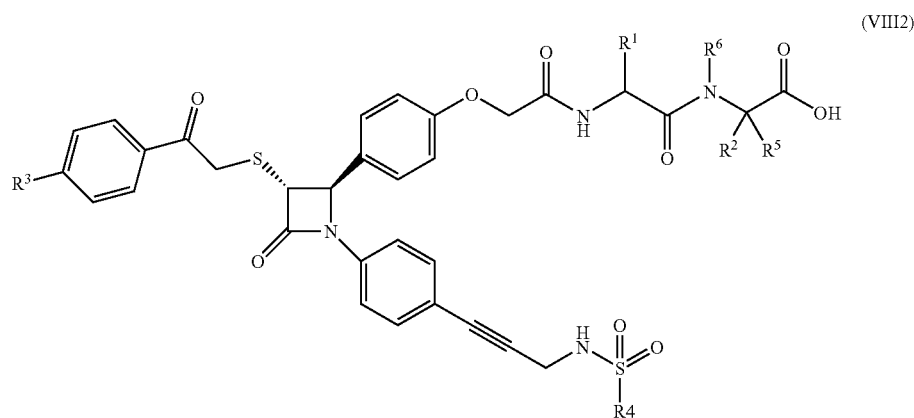

Process 5): Reacting a Compound of Formula (IX2):

Process 6): Reacting a Compound of Formula (XI2):

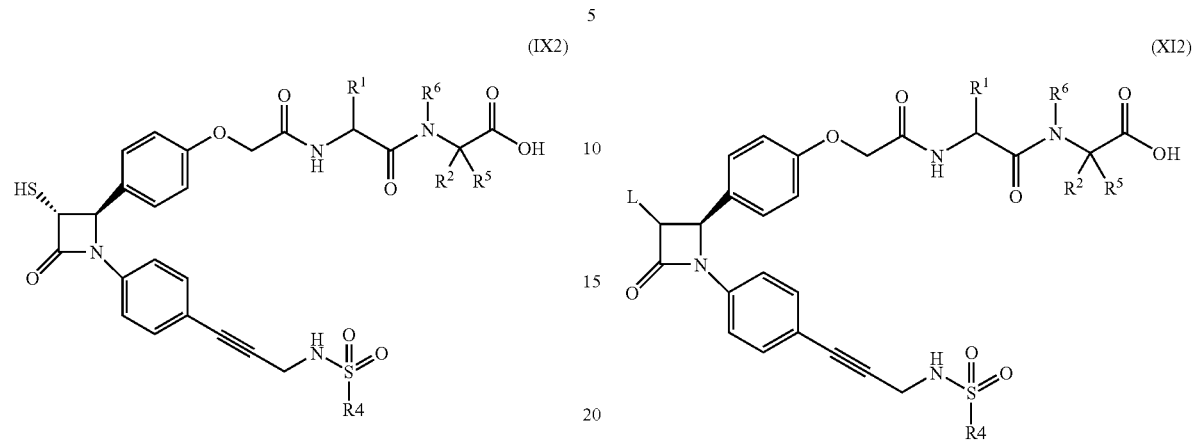

with a compound of formula (X):

wherein L is a displaceable group; with a compound of formula (XII):

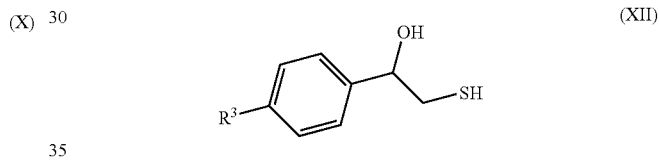

wherein L is a displaceable group;

Process 7): De-Esterifying a Compound of Formula (XIII2)

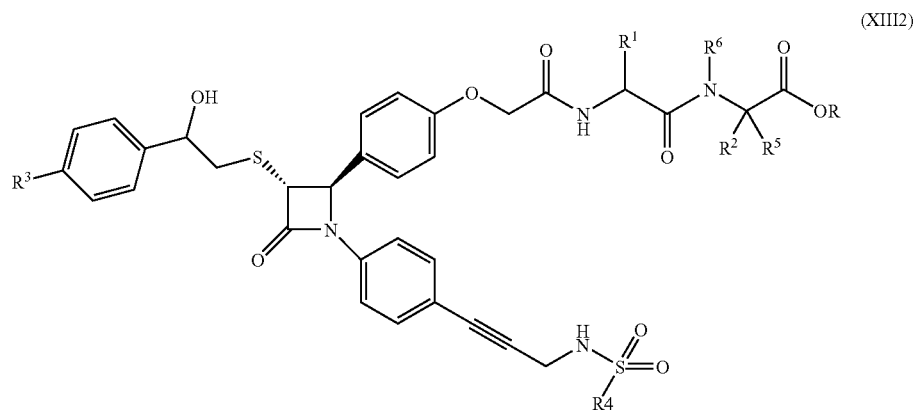

wherein the group C(O)OR is an ester group;

and thereafter if necessary or desirable:

i) converting a compound of the formula (I2) into another compound of the formula (I2);

ii) removing any protecting groups;
iii) forming a pharmaceutically acceptable salt, solvate, solvate of such a salt or a prodrug; or
iv) separating two or more enantiomers.

L is a displaceable group, suitable values for L are for example, a halogeno or sulphonyloxy group, for example a chloro, bromo, methanesulphonyloxy or toluene-4-sulphonyloxy group.

C(O)OR is an ester group, suitable values for C(O)OR are methoxycarbonyl, ethoxycarbonyl, t-butoxycarbonyl and benzyloxycarbonyl.

The starting materials used in the present invention can be prepared by modifications of the routes described in EP 0 792 264 B1, WO05062824 and WO. Alternatively they can be prepared by the following reactions.

Process 1): Alcohols of formula (II) or (II2) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Process 2) and Process 3): Acids and amines may be coupled together in the presence of a suitable coupling reagent. Standard peptide coupling reagents known in the art can be employed as suitable coupling reagents, for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Acids of formula (IV) or (IV2) and (VI) or (VI2) may be prepared from compounds of formula (II) or (II2) by reacting them with the appropriate, optionally protected, side chain using the conditions of Process 1). Amines of formula (V) and (VII) are commercially available compounds, or they are known in the literature, or they are prepared by standard processes known in the art.

Process 4): Reduction of compounds of formula (VIII) or (VIII2) could be performed with a hydride reagent such as sodium borohydride in a solvent such as methanol at temperatures suitable between −20-40° C.

Compounds of formula (VIII) or (VIII2) can be prepared using the conditions of Process 1, Process 2 or Process 3 and appropriate modifications of descriptions in EP 0 792 264 B1, WO05062824 and WO 05061452.

Process 5) and Process 6): these compounds may be reacted together in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (IX) or (IX2) and (XI) or (XI2) may be prepared by appropriate modifications of descriptions in EP 0 792 264 B1, WO05062824 and WO 05061452. Compounds of formula (X) and (XII) are commercially available compounds, or they are known in the literature, or they are prepared by standard processes known in the art. Process 7): Esters of formula (XIII) or (XIII2) may be deprotected under standard conditions such as those described below, for example a methyl or ethyl ester may be deprotected with sodium hydroxide in methanol at room temperature.

Compounds of formula (XIII) or (XIII2) may be prepared by a modification of any of the processes described herein for the preparation of compounds of formula (I) or (I2).

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess cholesterol absorption inhibitory activity. These properties may be assessed, using the following biological tests.

In Vivo Testing of Cholesterol Absorption Inhibitors (A)

C57BL/6 female mice were maintained on regular chow diet and housed in individual cages to collect faeces. Mice were fasted for 3 hours and then gavaged with vehicle or compound. Half an hour later the mice were gavaged with radiolabelled cholesterol. Six hours after the $^{14}$C-cholesterol gavage blood samples were taken via the tail and plasma prepared to determine how much cholesterol were absorbed. 24 hours after the gavage of $^{14}$C-cholesterol the mice were bled and plasma were prepared for analysis. Faeces were collected for 24 hours to assess absorption efficiency.

In Vivo Testing of Cholesterol Absorption Inhibitors (B).

C57BL/6 female mice were maintained on regular chow diet and housed in individual cages to collect faeces. Mice were fasted for 3 hours and then gavaged with vehicle or compound. One to ten hours later the mice were gavaged with radiolabelled cholesterol. Six hours after the $^{14}$C-cholesterol gavage blood sample was taken via the tail and plasma prepared to determine how much cholesterol was absorbed. 24 hours after the gavage of $^{14}$C-cholesterol the mice were bled and plasma analysed for radioactivity. Faeces were also collected for 24 hours to assess absorption efficiency.

References
1. E. A. Kirk, G. L. Moe, M. T. Caldwell, J. A. Lermnark, D. L. Wilson, R. C. LeBoeuf. Hyper- and hypo-responsiveness to dietary fat and cholesterol among inbred mice: searching for level and variability genes. J. Lipid Res. 1995 36:1522-1532.
2. C. P. Carter, P. N. Howles, D. Y. Hui. Genetic variation in cholesterol absorption efficiency among inbred strains of mice. J. Nutr. 1997 127:1344-1348.
3. C. D. Jolley, J. M. Dietschy, S. D. Turley. Genetic differences in cholesterol absorption in 129/Sv and C57BL/6 mice: effect on cholesterol responsiveness. Am. J. Physiol. 1999 276:G1117-G1124.

Administration of 0.2 μmol/kg of Example 6 gave 90% inhibition of $^{14}$C-cholesterol absorption (procedure A).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range of approximately 0.02-100 mg/kg, preferably 0.02-50 mg/kg, and this normally provides a therapeutically-effective dose. A unit dose form such as a tablet or capsule will usually contain, for example 1-250 mg of active ingredient. Preferably a daily dose in the range of 1-50 mg/kg, particularly 0.1-10 mg/kg is employed. In another aspect a daily dose in the rage of 0.01-20 mg/kg is employed. In one aspect of the invention the daily dose of a compound of formula (I) is less than or equal to 100 mg. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective cholesterol absorption inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of a cholesterol absorption inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the production of a cholesterol absorption inhibitory effect in a warm-blooded animal, such as man.

Herein, where the production of a cholesterol absorption inhibitory effect or a cholesterol lowering effect is stated, suitably this relates to the treatment of hyperlipidaemic conditions in a warm-blooded animal, such as man. Additionally is relates to the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man. Furthermore it relates to the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man. It also relates to the treatment of atherosclerosis, coronary heart diseases, myocardial infarction, angina pectoris, peripheral vascular diseases, stroke and transient ischaemic attacks in a warm-blooded animal, such as man.

The production of a cholesterol absorption inhibitory effect or a cholesterol lowering effect also relates to a method of treating and/or preventing atherosclerotic lesions, a method of preventing plaque rupture and a method of promoting lesion regression. Furthermore it relates to a method of inhibiting monocytes-macrophage accumulation in atherosclerotic lesions, a method of inhibiting expression of matrix metalloproteinases in atherosclerotic lesions, a method of inhibiting the destabilization of atherosclerotic lesions, a method for preventing atherosclerotic plaque rupture and a method of treating unstable angina.

The production of a cholesterol absorption inhibitory effect or a cholesterol lowering effect also relates to a method of treating sitosterolemia.

Compounds of formula (I), or a pharmaceutically acceptable salt, solvate, solvate of such a salt or a prodrug thereof may also have value in the treatment or prevention of Alzheimer's Disease (see for example WO 02/096415). Therefore in a further aspect of the invention, there is provided a compound of formula (I), or a pharmaceutically acceptable salt, solvate, solvate of such a salt or a prodrug thereof, for use in the treatment or prevention of Alzheimer's Disease.

Compounds of formula (I), or a pharmaceutically acceptable salt, solvate, solvate of such a salt or a prodrug thereof may also have value in the treatment or prevention of cholesterol associated tumors. Therefore in a further aspect of the invention, there is provided a compound of formula (I), or a pharmaceutically acceptable salt, solvate, solvate of such a salt or a prodrug thereof, for use in the treatment or prevention of cholesterol associated tumors.

Compounds of formula (I), or a pharmaceutically acceptable salt, solvate, solvate of such a salt or a prodrug thereof may also have value in the treatment or prevention of vascular inflammation (see for example WO 03/026644). Therefore in a further aspect of the invention, there is provided a compound of formula (I), or a pharmaceutically acceptable salt, solvate, solvate of such a salt or a prodrug thereof, for use in the treatment or prevention of vascular inflammation.

According to a further feature of this aspect of the invention there is provided a method for producing a cholesterol absorption inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

The cholesterol absorption inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional cholesterol absorption inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with cholesterol biosynthesis inhibitors, or pharmaceutically acceptable salts, solvates, solvates of such salts or prodrugs thereof. Suitable cholesterol biosynthesis inhibitors include HMG Co-A reductase inhibitors, squalene synthesis inhibitors and squalene epoxidase inhibitors. Suitable squalene synthesis inhibitors are e.g squalestatin 1, TAK 475 and compounds described in WO2005012284. A suitable squalene epoxidase inhibitor is NB-598.

In this aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and rosuvastatin, or a pharmaceutically acceptable salt, solvate, solvate of such a salt or a prodrug thereof. A further particular statin is pitavastatin, or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is rosuvastatin, or a pharmaceutically acceptable salt, solvate, solvate of such a salt or a prodrug thereof. A preferable particular statin is rosuvastatin calcium salt.

Therefore in an additional feature of the invention, there is provided a combination of a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of a cholesterol lowering effect.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a matrix metalloproteinase inhibitor.

In another aspect of the invention, the compound of formula (I), or a pharmaceutically acceptable salt, solvate, solvate of such a salt or a prodrug thereof, may be administered in association with an ileal bile acid (IBAT) inhibitor or a pharmaceutically acceptable salt, solvate, solvate of such a salt or a prodrug thereof. Suitable compounds possessing IBAT inhibitory activity for use in combination with compounds of the present invention have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 00/35889, WO 01/34570, WO 00/38725, WO 00/38726, WO 00/38727, WO 00/38728, WO 00/38729, WO 00/47568, WO 00/61568, WO 01/66533, WO 01/68096, WO 01/68637, WO 02/08211, WO 02/50051, WO 03/018024, WO 03/040127, WO 03/043992, WO 03/061604, WO 04/020421, WO 04/076430, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 864 582, EP 869 121 and EP 1 070 703, WO 03/020710, WO 03/022825, WO 03/022830, WO 03/022286, WO 03/091232, WO 03/106482, and EP 597 107 and the contents of these patent applications are incorporated herein by reference. Particularly the named examples of these patent applications are incorporated herein by reference. More particularly claim 1 of these patent application are incorporated herein by reference.

Other suitable classes of IBAT inhibitors for use in combination with compounds of the present invention are the benzothiepines, 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity for use in combination with compounds of the present invention is (3R,5R)-3-butyl-3-ethyl-1,1-dioxido-5-phenyl-2,3,4,5-tetrahydro-1,4-benzothiazepin-8-yl beta-D-glucopyranosiduronic acid (EP 864 582).

A further suitable compound possessing IBAT inhibitory activity for use in combination with compounds of the present invention is S-8921 (EP 597 107) and BARI-1741.

A further suitable IBAT inhibitor for use in combination with compounds of the present invention is the compound:

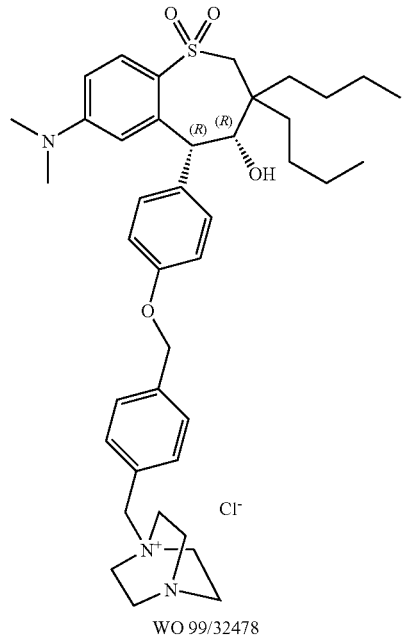

WO 99/32478

A particular IBAT inhibitor for use in combination with compounds of the present invention is selected from any one of Examples 1-120 of WO 02/50051, or a pharmaceutically acceptable salt, solvate, solvate of such a salt or a prodrug thereof, and the compounds of Examples 1-120 are incorporated herein by reference. Claims 1-15 of WO 02/50051 are also incorporated herein by reference. A particular IBAT inhibitor selected from WO 02/50051 for use in combination with compounds of the present invention is selected from any one of:

1,1-dioxo-3,3-dibutyl-5-phenyl-7-methylthio-8-(N-{(R)-1'-phenyl-1'-[N'-(carboxymethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)—N'-(2-methylsulphinyl-1-carboxyethyl)carbamoyl]benzyl}carbamoylmethoxy)-2,3,4,5-tetrahydro-1,5-benzothiazepine; and 1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-44 of WO 03/020710, or a pharmaceutically acceptable salt, solvate, solvate of such a salt or a prodrug thereof, and the compounds of Examples 1-44 are incorporated herein by reference. Claims 1-10 of WO 03/020710 are also incorporated herein by reference. A particular MBAT inhibitor selected from WO 03/020710 for use in combination with compounds of the present invention is selected from any one of:

1,1-dioxo-3,3-dibutyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-((S)-1-carbamoyl-2-hydroxyethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(hydroxycarbamoylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N-((R)-α-{N'-[2-(N'-pyrimidin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-[N-((R)-α-{N'-[2-(N'-pyridin-2-ylureido)ethyl]carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-(N-{(R)-α-[N'-(1-t-butoxycarbonylpiperidin-4-ylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[1-(2,3-dihydroxypropyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-[N-(R)-α-{N'-[2-(3,4-dihydroxyphenyl)-2-methoxyethyl]carbamoyl}benzyl)carbamoylmethoxy]-2,3,4,5-tetrahydro-1,5-benzothiazepine 1,1-dioxo-3-butyl-3-ethyl-5-phenyl-7-methylthio-8-(N-{(R)-α-[N'-(2-aminoethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(piperidin-4-ylmethyl)carbamoyl]benzyl}carbamoylmethoxy)-2,3,4,5-tetrahydro-1,5-benzothiazepine; or 1,1-dioxo-3-butyl-3-ethyl-5-phenyl-7-methylthio-8-(N-{(R)-α-[N'-(2-N,N-dimethylaminosulphamoylethyl)carbamoyl]benzyl}carbamoylmethoxy)-2,3,4,5-tetrahydro-1,5-benzothiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/022825, or a pharmaceutically acceptable salt, solvate, solvate of such a salt or a prodrug thereof, and the compounds of Examples 1-7 are incorporated herein by reference. Claims 1-8 of WO 03/022825 are also incorporated herein by reference. A particular IBAT inhibitor selected from WO 03/022825 for use in combination with compounds of the present invention is selected from any one of:

1,1-dioxo-3(R)-3-butyl-3-ethyl-5-(R)-5-phenyl-8-[N-((R)-α-carboxybenzyl)carbamoylmethoxy]-2,3,4,5-tetrahydro-1,4-benzothiazepine;

1,1-dioxo-3(S)-3-butyl-3-ethyl-5-(S)-5-phenyl-8-[N-((R)-α-carboxybenzyl)carbamoylmethoxy]-2,3,4,5-tetrahydro-1,4-benzothiazepine;

1,1-dioxo-3(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine;

1,1-dioxo-3(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-(S)-3-ethyl-3-butyl-4-hydroxy-5-(S)-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-dioxo-3-(R)-3-ethyl-3-butyl-4-hydroxy-5-(R)-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,4-benzothiazepine ammonia salt;

1,1-dioxo-3-(S)-3-ethyl-3-butyl-5-(S)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt; and 1,1-dioxo-3-(R)-3-ethyl-3-butyl-5-(R)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt;

or a pharmaceutically acceptable salt, solvate, solvate of such a salt or a prodrug thereof.

A particular IBAT inhibitor for use in combination with compounds of the present invention is selected from any one of Examples 1-4 of WO 03/022830, or a pharmaceutically acceptable salt, solvate, solvate of such a salt or a prodrug thereof, and the compounds of Examples 1-4 are incorporated herein by reference. Claims 1-8 of WO 03/022830 are also incorporated herein by reference. A particular IBAT inhibitor selected from WO 03/022830 for use in combination with compounds of the present invention is selected from any one of:

1,1-dioxo-3-butyl-3-ethyl-4-hydroxy-5-phenyl-7-(N-{(R)-α-[N-(carboxymethyl)carbamoyl]benzyl}carbamoylmethylthio)-2,3,4,5-tetrahydrobenzothiepine 1,1-dioxo-3-butyl-3-ethyl-4-hydroxy-5-phenyl-7-(N-{(R)-α-[N-(2-sulphoethyl)carbamoyl]-4-hydroxybenzyl}carbamoylmethylthio)-2,3,4,5-tetrahydrobenzothiepine ammonia salt 1,1-dioxo-3-butyl-3-ethyl-4-hydroxy-5-phenyl-7-{N-[α-(carboxy)-2-fluorobenzyl]carbamoylmethylthio}-2,3,4,5-tetrahydrobenzothiepine; and 1,1-dioxo-3-butyl-3-ethyl-4-hydroxy-5-phenyl-7-{N-[1-(carboxy)-1-(thien-2-yl)methyl]carbamoylmethylthio}-2,3,4,5-tetrahydrobenzothiepine or a pharmaceutically acceptable salt, solvate, solvate of such a salt or a prodrug thereof.

A particular IBAT inhibitor for use in combination with compounds of the present invention is selected from any one of Examples 1-39 of WO 03/022286, or a pharmaceutically acceptable salt, solvate, solvate of such a salt or a prodrug thereof, and the compounds of Examples 1-39 are incorporated herein by reference. Claims 1-10 of WO 03/022286 are also incorporated herein by reference. A particular IBAT inhibitor selected from WO 03/022286 for use in combination with compounds of the present invention is selected from any one of:

1,1-dioxo-3,3-dibutyl-5-phenyl-7-methylthio-8-(N-{(R)-α-[N-((R)-1-carboxy-2-methylthioethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N—((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine;

or a pharmaceutically acceptable salt, solvate, solvate of such a salt or a prodrug thereof.

A particular IBAT inhibitor for use in combination with compounds of the present invention is selected from any one of Examples 1-7 of WO 03/091232, or a pharmaceutically acceptable salt, solvate, solvate of such a salt or a prodrug thereof, and the compounds of Examples 1-7 are incorporated herein by reference. Claims 1-10 of WO 03/091232 are also incorporated herein by reference. A particular IBAT inhibitor selected from WO 03/091232 for use in combination with compounds of the present invention is selected from any one of:

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-{N-[(R)-α-(N-{2-(S)—[N-(carbamoylmethyl)carbamoyl]pyrrolidin-1-ylcarbonylmethyl}carbamoyl)benzyl]carbamoylmethoxy}-2,3,4,5-tetrahydro-1,2,5-benzothiadiazepine;

1,1-Dioxo-3,3-dibutyl-5-phenyl-7-methylthio-8-[N-((R)-α-{N-[2-(3,4,5-trihydroxyphenyl)ethyl]carbamoyl}benzyl)carbamoylmethoxy]-2,3,4,5-tetrahydro-1,2,5-benzothiadiazepine; and 1,1-Dioxo-3,3-dibutyl-5-phenyl-7-methylthio-8-(N-{(R)-α-[N-(2-(R)-3-(S)-4-(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof. Further suitable compounds possessing IBAT inhibitory for use in combination with compounds of the present invention are disclosed in WO 03/106482

Suitable IBAT inhibitors having the above structure for use in combination with compounds of the present invention are selected from any one of:

1,1-dioxo-3,3-dibutyl-5-phenyl-7-methylthio-8-(N-{(R)-α-[N'-((S)-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylthioethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylsulphinylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methoxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylthiopropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine; or 1,1-dioxo-3,3-dibutyl-5-phenyl-7-methylthio-8-(N-{(R)-α-[N'-((S)-1-carboxyethyl)carbamoyl]benzyl}carbamoylmethoxy)-2,3,4,5-tetrahydro-1,5-benzothiazepine.

or a pharmaceutically acceptable salt, solvate, solvate of such a salt or a prodrug thereof.

Further suitable IBAT inhibitors for use in combination with compounds of the present invention are those disclosed in WO 04/076430.

In a particular aspect of the invention an IBAT inhibitor or a pharmaceutically acceptable salt, solvate, solvate of such a salt or a prodrug thereof is an IBAT inhibitor or a pharmaceutically acceptable salt thereof.

Therefore in an additional feature of the invention, there is provided a combination of a compound of formula (I), or a pharmaceutically acceptable salt, solvate, solvate of such a salt or a prodrug thereof and an IBAT inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an IBAT inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) an IBAT inhibitor, or a pharmaceutically acceptable salt, solvate, solvate of such a salt or a prodrug thereof, in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) an IBAT inhibitor, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in the manufacture of a medicament for use in the production of a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt or solvate thereof, or a solvate of such a salt, may be administered in association with a peroxisome proliferator-activated receptor (PPAR) modulating agent. PPAR modulating agents include a PPAR alpha and/or gamma and/or delta agonist, or pharmaceutically acceptable salts, solvates, solvates of such salts or prodrugs thereof. Suitable PPAR alpha and/or gamma and/or delta agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO 04/000790, WO 04/000295, WO 04/000294, WO 03/051822, WO 03/051821, WO 02/096863, WO 04/056748, WO 03/051826, WO 02/085844, WO 01/40172, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma and/or delta agonist refers to muraglitazar (BMS 298585), rivoglitazone (CS-011), netoglitazone (MCC-555), balaglitazone (DRF-2593, NN-2344), clofibrate (Atromid-S®), fenofibrate, bezafibrate (Oralipin®), gemfibrozil (Lopid®), ciprofibrate (Ciprol®), pioglitazone (Actos®), rosiglitazone (Avandia®), AVE-0847, AVE-8134, CLX-0921, DRF-10945, DRF-4832, E-3030, K-111, KRP-101, LBM-642 (oxeglitazar), LY-518674, LY-674, naveglitazar (LY-818), LY-929, 641597, GW-590735, GW-677954, GW-501516, metaglidasan (MBX-102), MBX-2044, ONO-5129, PLX-204, R-483 (BM131258), R-119702, T-131 (AMG-131), TAK-559 or TAK-654. Particularly a PPAR alpha and/or gamma and/or delta agonist refers to tesaglitazar ((S)-2-ethoxy-3-[4-(2-{4-methanesulphonyloxyphenyl}ethoxy)phenyl]propanoic acid) and pharmaceutically acceptable salts thereof.

For instance, a PPAR alpha and/or gamma and/or delta agonist refers to (S)-2-ethoxy-3-[4-(2-{4-methanesulphonyloxyphenyl}ethoxy)phenyl]propanoic acid (tesaglitazar) and pharmaceutically acceptable salts thereof.

Therefore in an additional feature of the invention, there is provided a combination of a compound of formula (I), or a pharmaceutically acceptable salt, solvate, solvate of such a salt or a prodrug thereof and a PPAR alpha and/or gamma agonist, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma and/or delta agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) a PPAR alpha and/or gamma and/or delta agonist, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a PPAR alpha and/or gamma and/or delta agonist, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma and/or delta agonist, or a pharmaceutically acceptable salt, solvate, solvate of such a salt or a prodrug thereof, in the manufacture of a medicament for use in producing a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma and/or delta agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an -agonists to the receptor HM74A (nicotinic acid receptor). HM74A receptor agonists may be nicotine acid derivates. As used herein "nicotinic acid derivative" means a compounds comprising a pyridine-3-carboxylate structure or a pyrazine-2-carboxylate structure. Examples of nicotinic acid derivatives include nicotinic acid, niceritrol, nicofuranose, NIASPAN® and acipimox.

HM74A receptor agonists may be anthranilic acid derivatives described in WO-2005016867 and WO-2005016870.

Other nicotinic receptor agonists are for example compounds described in WO2005011677, WO2004032928 and WO2004033431.

Therefore, in an additional feature of the invention, there is provided a combination of a compound of formula (I), or a pharmaceutically acceptable salt, solvate, solvate of such a salt or a prodrug thereof and a HM74A receptor agonists or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a HM74A receptor agonists, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a HM74A receptor agonists, or a pharmaceutically acceptable salt, solvate, solvate of such a salt or a prodrug thereof, in association with a pharmaceutically acceptable diluent or carrier.

In another aspect of the invention, there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a mediator of reverse cholesterol transport i.e. a peptide (Apo A-1 mimetic peptides) or small molecule mediator of reverse cholesterol transport e.g. those described in Circ. 2002; 105:290, Circ. 2004.109:3215, Curr. Opinion in Lipidology 2004, 15:645 or in WO2004094471.

In another aspect of the invention, the compound of formula I, or a pharmaceutically acceptable salt or solvate thereof, or a solvate of such a salt, may be administered in association with an anti-obesity compound, or pharmaceutically acceptable salts, solvates, solvates of such salts or prodrugs thereof, for example a pancreatic lipase inhibitor e.g. orlistat (EP 129,748) or an appetite (satiety) controlling substance for example sibutramine (GB 2,184,122 and U.S. Pat. No. 4,929,629), a cannabinoid 1 (CB1) antagonist or inverse agonist, or pharmaceutically acceptable salts, solvates, solvates of such salts or prodrugs thereof, for example rimonabant (EP 656354) and as described in WO01/70700 or a melanin concentrating hormone (MCH) antagonist, or pharmaceutically acceptable salts, solvates, solvates of such salts or prodrugs thereof, for example as described in WO 04/004726.

According to another feature of the invention there is provided the use of a compound of the formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula (I), or a pharmaceutically acceptable salt, solvate, solvate of such a salt or a prodrug thereof, may be administered in association with a bile acid sequestrant or a pharmaceutically acceptable salt, solvate, solvate of such a salt or a prodrug thereof. Suitable bile acid sequestrants include cholestyramine, cholestipol and cosevelam hydrochloride.

Therefore, in an additional feature of the invention, there is provided a combination of a compound of formula (I), or a pharmaceutically acceptable salt, solvate, solvate of such a salt or a prodrug thereof and a bile acid sequestrant or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid sequestrant, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula I, or a pharmaceutically acceptable salt or solvate thereof, or a solvate of such a salt, may be administered in association with a cholesteryl ester transfer protein (CETP) inhibitor, or pharmaceutically acceptable salts, solvates, solvates of such salts or prodrugs thereof, for example JTT-705, torcetrapib (CP-529414), Bay 194789 and those referenced and described in WO05033082 or WO 00/38725 page 7 line 22-page 10, line 17 which are incorporated herein by reference.

In another aspect of the invention, the compound of formula I, or a pharmaceutically acceptable salt or solvate thereof, or a solvate of such a salt, may be administered in association with a acyl coenzymA: cholesterol O-acyltransferase (ACAT) inhibitor, or pharmaceutically acceptable salts, solvates, solvates of such salts or prodrugs thereof, for example pactimibe (CS-505), eflucimibe (F-12511) and SMP-797, avasimibe or K604.

In yet another aspect of the invention, the compound of formula I, association with modulators for example GW-4064 and INT-747 of nuclear receptors such as farnesoid or a pharmaceutically acceptable salt or solvate thereof, or a solvate of such a salt, may be administered in X receptor (FXR), or pharmaceutically acceptable salt, solvate, solvate of such a salt or a prodrug thereof.

In another aspect of the invention, the compound of formula I, or a pharmaceutically acceptable salt or solvate thereof, or a solvate of such a salt, may be administered in association with a phytosterol compound, or pharmaceutically acceptable salts, solvates, solvates of such salts or prodrugs thereof, for example stanols. An example of phytosterol analogs is FM-VP4.

In another aspect of the invention, the compound of formula I, or a pharmaceutically acceptable salt or solvate thereof, or a solvate of such a salt, may be administered in association with other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt or solvate thereof, or a solvate of such a salt, may be administered in association with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from Group X:

an antihypertensive compound (for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzemine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate and bevantolol hydrochloride);

an angiotensin converting enzyme inhibitor (for example alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat);

an angiotensin II receptor antagonist (for example candesartan, candesartan cilexetil, losartan, valsartan, irbesartan, tasosartan, telmisartan and eprosartan);

an andrenergic blocker (for example bretylium tosylate, dihydroergotamine so mesylate, phentolamine mesylate, solypertine tartrate, zolertine hydrochloride, carvedilol or labetalol hydrochloride); an alpha andrenergic blocker (for example fenspiride hydrochloride, labetalol hydrochloride, proroxan and alfuzosin hydrochloride); a beta andrenergic blocker (for example acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol); or a mixed alphalbeta andrenergic blocker;

an andrenergic stimulant (for example combination product of chlorothiazide and methyldopa, the combination product of methyldopa hydrochlorothiazide and methyldopa, clonidine hydrochloride, clonidine, the combination product of chlorthalidone and clonidine hydrochloride and guanfacine hydrochloride);

channel blocker, for example a calcium channel blocker (for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil);

a diuretic (for example the combination product of hydrochlorothiazide and spironolactone and the combination product of hydrochlorothiazide and triamterene);

anti-anginal agents (for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride);

vasodilators for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol and verapamil);

anti-coagulants (selected from argatroban, bivalirudin, dalteparin sodium, desirudin, dicumarol, Iyapolate sodium, nafamostat mesylate, phenprocoumon, tinzaparin sodium and warfarin sodium);

antithrombotic agents (for example anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab and zolimomab aritox);

fibrinogen receptor antagonists (for example roxifiban acetate, fradafiban, orbofiban, lotrafiban hydrochloride, tirofiban, xemilofiban, monoclonal antibody 7E3 and sibrafiban)

platelet inhibitors (for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole);

platelet aggregation inhibitors (for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban)

hemorrheologic agents (for example pentoxifylline);

lipoprotein associated coagulation inhibitors;

Factor VIIa inhibitors;

Factor Xa inhibitors;

low molecular weight heparins (for example enoxaparin, nardroparin, dalteparin, certroparin, pamaparin, reviparin and tinzaparin);

liver X receptor (LXR) agonists for example GW-3965 and those described in WO00224632, WO00103705, WO02090375 and WO00054759 (claim 1 and the named examples of these four application are incorporated herein by reference);

microsomal triglyceride transfer protein inhibitors for example implitapide, CP-346086, JTT-130, BMS-201038, R-103757 and those described in WO05/021486, WO03004020, WO03002533, WO02083658 and WO 00242291 (claim 1 and the named examples of these four application are incorporated herein by reference);

ApoA1 expression inducer for example those described in WO2005032559 or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Therefore, in an additional feature of the invention, there is provided a combination of a compound of formula (I), or a pharmaceutically acceptable salt, solvate, solvate of such a salt or a prodrug thereof and a compound from Group X or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a compound from Group X, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in the manufacture of a medicament for use in the production of a cholesterol lowering effect in a warm-blooded animal, such as man.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of cholesterol absorption in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18-25° C., with solvents of HPLC grade under anhydrous conditions, unless otherwise stated;

(iii) column chromatography (by the flash procedure) was performed on Silica gel 40-63 µm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CDCl_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer unless otherwise stated data was recorded at 400 MHz; and peak multiplicities are shown as follows: s, singlet; d, doublet; dd, double doublet; t, triplet; tt, triple triplet; q, quartet; tq, triple quartet; m, multiplet; br, broad; ABq, AB quartet; ABd, AB doublet, ABdd, AB doublet of doublets; dABq, doublet of AB quartets;

Mass spectra were recorded on one of the following instruments: LCT, QTOF, ZQ Mass spectrometer, all from Waters.

LC-MS:

Separation was performed using Agilent 1100 Series Modules or Waters 1525 pump on a Synergi MAX-RP (Phenomenex) C12 3×50 mm 4 μm with gradient elution.

Samples were injected using Waters 2700 Sample Manager.

Mobile phases:

Generic gradients were applied from 5% to 95% acetonitrile. Buffers containing 10 mM ammonium acetate or 5 mM ammonium formiate/5 mM formic acid were used.

The mass spectra were recorded with a Waters ZQ2000 or Waters ZMD equipped with an electrospray interface, swithing positive and negative ionization mode. UV spectra were collected by a Agent 1100 PDA or Waters 2996 DAD and the evaporative light scattering (ELS) signal by a Sedere Sedex 55 or 75.

Data collection and evaluation were performed using the MassLynx software.

Accurate mass data were determined using either a LCT or QTOF MS (Waters) with leucine enkephaline (m/z 556.2771) as lockmass. Unless otherwise stated the mass ion quoted is (MH$^+$).

Unless further details are specified in the text, analytical high performance liquid chromatography (HPLC) was performed on Prep LC 2000 (Waters), Cromasil C$_8$, 7 μM, (Akzo Nobel); MeCN and de-ionised water 10 mM ammonium acetate as mobile phases, with suitable composition;

(vii) intermediates were not generally fully characterised and purity was assessed by thin layer chromatography (TLC), HPLC, infra-red (IR), MS or NMR analysis;

(viii) where solutions were dried sodium sulphate was the drying agent; and (ix) the following abbreviations may be used hereinbefore or hereinafter:

DCM dichloromethane;
DMF N,N-dimethylformamide;
TBTU o-Benzotriazol-1-yl-N,N,N',N'-tetramethyluronium tetrafluoroborate;
EtOAc ethyl acetate;
MeCN acetonitrile;
TFA trifluoroacetic acid;
DMAP 4-(dimethylamino)pyridine;
BSA N,O-Bis(trimethylsilyl)acetamide; and
TBAF tetrabutylammonium fluoride;
NMM N-methyl morpholine;
TEA triethylamine;
DBN 1,5-diazabicyclo-[4,3,0]-non-5-ene.

EXAMPLES

Example 1

N-({4-[(2R,3R)-3-{[(2R)-2-(4-fluorophenyl)-2-hydroxyethyl]thio}-1-(4-{3-[(methylsulfonyl)amino] prop-1-yn-1-yl}phenyl)-4-oxoazetidin-2-yl] phenoxy}acetyl)glycyl-3-cyclohexyl-D-alanine N-({4-[(2R,3R)-3-{[(2R)-2-{[tert-butyl(dimethyl)silyl] oxy}-2-(4-fluorophenyl)ethyl]thio}-1-(4-{3-[(methylsulfonyl)amino]prop-1-yn-1-yl}phenyl)-4-oxoazetidin-2-yl] phenoxy}acetyl)glycyl-3-cyclohexyl-D-alanine (16.7 mg, 0.018 mmol) (Method 1) was dissolved in acetic acid (1 ml). Water (0.100 ml) and LiCl (50 mg, 1.18 mmol) were added and the reaction mixture was stirred overnight. The acetic acid was co-evaporated with toluene. The residue was purified with preparative HPLC on a C8 column, UV 235/285 nm. A gradient from 20 to 60% MeCN in 0.1M NH$_4$OAc buffer was used as eluent. The pure fractions were collected and some of MeCN was removed under reduced pressure. The residue was lyophilised to give the title compound. H-NMR (500 MHz, DMSO-d$_6$): 0.73-0.92 (m, 2H), 1.05-1.19 (m, 3H), 1.30 (b, 1H), 1.40-1.70 (m, 7H), 2.93 (d, 2H), 2.97 (s, 3H), 3.76 (d, 2H), 4.00 (s, 2H), 4.14 (bs, 1H), 4.31 (d, 1H), 4.52 (s, 2H), 4.71 (t, 1H), 5.10 (d, 1H), 5.74 (bs, 1H), 6.99 (d, 2H), 7.08-7.13 (m, 2H), 7.20 (d, 2H), 7.32-7.41 (m, 6H), 7.60 (b, 1H), 7.94 (b, 1H), 8.26 (t, 1H). M/z: 809 (M+1) and 807 (M−1).

Example 2

N-({4-[(2R,3R)-3-{[(2R)-2-(4-fluorophenyl)-2-hydroxyethyl]thio}-1-(4-{3-[(methylsulfonyl)amino] prop-1-yn-1-yl}phenyl)-4-oxoazetidin-2-yl] phenoxy}acetyl)glycyl-D-valine To a stirred solution of {4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetic acid (19.4 mg, 0.027 mmol), and N-methylmorpholine (9 μl, 0.082 mmol) in DMF (1 ml, dry) was added. TBTU (12 mg, 0.037 mmol) and the reaction mixture was stirred at 30° C. for 1 hour. Glycyl-D-valine hydrochloride (8.0 mg, 0.038 mmol) was added and the reaction mixture was stirred for 1 hour. LC-MS showed the formation of the TBDMS-ether of the title compound, M/z: 868.68 (M−1). The reaction mixture was diluted with water and EtOAc. The solution was acidified with KHSO$_4$ (2M) to pH ca 3. The phases were separated and the organic phase was concentrated. The residue was dissolved in acetic acid (1 ml). Water (100 μl) and LiCl (51.4 mg, 1.21 mmol) were added and the reaction mixture was stirred over the weekend. The acetic acid was co-evaporated with toluene. The residue was purified with preparative HPLC on a C8 column, UV 235/285 nm. A gradient from 20 to 80% MeCN in 0.1M NH$_4$OAc buffer was used as eluent. The pure fractions were collected and most of the MeCN was removed under reduced pressure. The residue was diluted with water and DCM. It was acidified with KHSO$_4$ (2M) to pH 3. The phases were separated and the organic phase was passed through a phase separator. The organic phase was concentrated and the residue was dissolved in MeCN and water. After lyophilisation, the title compound was obtained. H-NMR (500 MHz, DMSO-d$_6$): 0.84 (d, 3H), 0.86 (d, 3H), 1.99-2.06 (m, 1H), 2.92 (d, 2H), 2.97 (s, 3H), 3.79-3.88 (m, 2H), 4.01 (d, 2H), 4.12-4.17 (m, 1H), 4.29 (d, 1H), 4.53 (s, 2H), 4.71 (t, 1H), 5.10 (d, 1H), 5.65 (bs, 1H), 6.99 (d, 2H), 7.08-7.13 (m, 2H), 7.20 (d, 2H), 7.30-7.40 (m, 6H), 7.58 (t, 1H), 8.02 (d, 1H), 8.24 (t, 1H), 12.65 (b, 1H). M/z: 753.52 (M−1).

Example 3

N-({4-[(2R,3R)-3-{[(2R)-2-(4-fluorophenyl)-2-hydroxyethyl]thio}-1-(4-{3-[(methylsulfonyl)amino] prop-1-yn-1-yl}phenyl)-4-oxoazetidin-2-yl] phenoxy}acetyl)glycyl-3-methyl-D-valine To a stirred solution of {4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetic acid (19.4 mg, 0.027 mmol) and N-methylmorpholine (9 μl, 0.082 mmol) in DMF (1 ml, dry) was added TBTU (13.0 m, 0.040 mmol) and the reaction mixture was stirred at 30° C. for 1 hour. Glycyl-3-methyl-D-valine (7.1 mg, 0.038 mmol) was added and the reaction mixture was stirred for 1 hour. LC-MS showed the formation of the TBDMS-ether of the title compound, M/z: 881.65 (M−1). The reaction mixture was diluted with water and EtOAc. The solution was acidified with KHSO$_4$ (2M) to pH 3. The phases were separated and the organic phase was concentrated. The residue was dissolved in acetic acid (1 ml). Water (100 µl) and LiCl (63 mg, 1.47 mmol) were added and the reaction mixture was stirred over the weekend. The acetic acid was co-evaporated with toluene. The residue was purified with preparative HPLC on a C8 column, UV 235/285 nm. A gradient from 20 to 60% MeCN in 0.1M NH$_4$OAc buffer was used as eluent. The pure fractions were collected and most of the MeCN was removed under reduced pressure. The residue was lyophilised to give the title compound. H-NMR (500 MHz, DMSO-d$_6$): 0.89 (s, 9H), 2.92 (d, 2H), 2.97 (s, 8H), 3.82 (d. 2H), 3.98-4.07 (b, 3H), 4.31 (d, 1H), 4.53 (s, 2H), 4.72 (t, 1), 5.09 (d, 1H), 6.99 (d, 2H), 7.07-7.13 (m, 2H), 7.20 (d, 2H), 7.32-7.40 (m, 6H), 7.59 (b, 1H), 7.81 (b, 1H), 8.23 (t, 1H). M/z: 769.39 (M+1) and 767.58 (M−1).

Example 4

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-D-lysine N-({4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetyl)glycyl-N$^6$-(tert-butoxycarbonyl)-D-lysine (Method 2) (21.9, 0.022 mmol) was dissolved in MeCN (1.5 ml). Cerium(4+) tetranitrate-nitric acid (1:2) diammoniate (25.1 mg, 0.046 mmol) and water (50 µl) were added. The reaction mixture was heated at 45° C. for 6 h and 30 minutes and it was allowed to stand at room temperature over the weekend. The solution was purified with preparative HPLC on a C8 column, UV 235/285 nm. A gradient from 10 to 90% MeCN in 0.1M NH$_4$OAc buffer was used as eluent. Most of the MeCN was removed under reduced pressure and the residue was lyophilised to give the title compound as a yellow solid. H-NMR (500 MHz, DMSO-d$_6$): 1.13-1.66 (m, 6H), 2.64-2.71 (m, 2H), 2.90-2.96 (m, 2H), 2.97 (s, 3H), 3.62-3.80 (m, 3H), 4.00 (s, 2H), 4.34 (d, 1H), 4.53 (s, 2H), 4.72 (t, 1H), 5.09 (d, 1H), 6.99 (d, 2H), 7.07-7.13 (m, 2H), 7.20 (d, 2H), 7.32-7.40 (m, 6H), 7.46 (b, 1H), 8.42 (t, 1H). M/z: 782.58 (M−1) and 784.42 (M+1).

Example 5

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycylglycine {4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetic acid (Method 8) (19.4 mg, 0.027 mmol) (9.7 mg, 0.014 mmol) was dissolved in DCM (1 ml, dry). Methyl glycylglycinate hydrochloride (3.1 mg, 0.017 mmol) followed by N-methylmorpholine (4 µl, 0.041 mmol) were added. TBTU (5.8 mg, 0.018 mmol) was added and the reaction mixture was stirred for 2 hours. LC-MS confirmed the formation of the methylester and TBDMS-ether of the title compound, M/z: 839.58 (M−1). The solvent was removed under reduced pressure. The residue was dissolved in MeCN (1 ml). Triethyamine (40 µl, 0.287 mmol), water (10 µl) and LiCl (23.6 mg, 0.55 mmol) were added and the reaction mixture was stirred over the weekend. LC-MS showed complete hydrolysis giving the TBDMS-ether of the title compound, M/z: 827.32 (M+1) and 825.56 (M−1). The solvent was removed under reduced pressure. The crude was dissolved in acetic acid (1 ml) and water (100 µl) and LiCl (27 mg, 0.64 mmol) were added. The reaction mixture was stirred for 6 hours and 30 minutes. Additional LiCl (30 mg, 0.71 mmol) and water (40 µl) were added and the reaction mixture was stirred overnight. The acetic acid was co-evaporated with toluene and the residue was purified with preparative HPLC on a C8 column. A gradient from 20 to 60% MeCN in a 0.1M NH$_4$OAc buffer was used as eluent. The pure fractions were collected and most of the MeCN was removed under reduced pressure. The residue was lyophilised to give a the title compound. 2.91-2.96 (m, 2H), 2.98 (s, 3H), 3.38 (d 2H), 3.74 (d, 2H), 4.01 (s, 2H), 4.33 (d, 1H), 4.55 (s, 2H), 4.72 (t, 1H), 5.10 (d, 1H), 7.01 (d, 2H), 7.11 (t, 2H), 7.21 (d, 2H), 7.32-7.42 (m, 6H), 7.47 (b, 1H), 8.37 (t, 1H). M/z: 713.33 (M+1) and 711.45 (M−1).

Example 6

N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycine {4-[(2R,3R)-3-{[(2R)-2-{[tert-butyl(dimethyl)silyl]oxy}-2-(4-fluorophenyl)ethyl]thio}-(4-{3-[(methylsulfonyl)amino]prop-1-yn-1-yl}phenyl)-4-oxoazetidin-2-yl]phenoxy}acetic acid (Method 8) (19.4 mg, 0.027 mmol) (19.0 mg, 0.020 mmol) was dissolved in DCM (2 ml). Methyl glycinate hydrochloride (4.1 mg, 0.033 mmol) and N-methylmorpholine (6 µl, 0.059 mmol) were added and the reaction mixture was stirred for five minutes. TBTU (9.5 mg, 0.029 mmol) was added and the mixture was stirred for 2 hours. The solvent was removed under reduced pressure. LC-MS confirmed the formation of the methylester and TBDMS-ether of the title compound. M/z: 782.55 (M−1). The residue was suspended in MeCN (1 ml). Triethylamine (27 µl, 0.19 mmol), water (7 µl) and LiCl (24.8 mg, 0.58 mmol) were added and the reaction mixture was stirred at 35° C. overnight. Additional triethylamine (15 µl, 0.11 mmol) and water (15 µl) were added and the reaction mixture was stirred at 35° C. for 5 hours. Additional MeCN (1 ml) was added and the reaction mixture was stirred overnight. The mixture was purified with preparative HPLC on a C8 column, UV 235/285 nm. A gradient from 20 to 85% MeCN in 0.1M NH$_4$OAc buffer was used as eluent. Most of the MeCN was removed under reduced pressure and the residue was acidified to pH 3 and extracted from DCM. The phases were separated and the organic phase was passed through a phase separator. The solvent was removed under reduced pressure. The residue was dissolved in water and MeCN and lyophilised. LC-MS confirmed the formation of the TBDMS-ether of the title compound, M/z: 768.60 (M−1). The residue was dissolved in acetic acid (1 ml). Water (100 µl) and LiCl (27.6 mg, 0.65 mmol) were added and the reaction mixture was stirred overnight. The acetic acid was co-evaporated with toluene. The residue was purified with preparative HPLC on a C8 column. A gradient from 20 to 75% MeCN in 0.1M NH$_4$OAc buffer was used as eluent. Most of the MeCN was removed under reduced pressure and the residue was lyophilised to give the title compound. H-NMR (400 MHz, DMSO-d$_6$) 2.93 (d, 2H), 2.98 (s, 3H), 3.47 (d, 2H), 4.01 (s, 2H), 4.32 (d, 1H), 4.50 (s, 2H), 4.72 8t, 1H), 5.10 (d, 1H), 7.00 (d, 2H), 7.11 (t, 2H), 7.21 (d, 2H), 7.32-7.42 (m, 6H), 7.79 (b, 1H). M/z: 654.43 (M−1).

Preparation of Starting Materials

Method 1

N-({4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetyl)glycyl-3-cyclohexyl-D-alanine {4-[(2R,3R)-3-{[(2R)-2-{[tert-butyl(dimethyl)silyl]oxy}-2-(4-fluorophenyl)ethyl]thio}-(4-{3-[(methylsulfonyl)amino]prop-1-yn-1-yl}phenyl)-4-oxoazetidin-2-yl]phenoxy}acetic acid (Method 8) (25.1 mg, 0.040 mmol) was dissolved in DMF (1 ml, dry). N-methylmorpholine (13 μl, 121 mmol) was added and the reaction mixture was stirred at 30° C. for five minutes. TBTU (20.1 mg, 0.063 mmol) was added and the reaction mixture was stirred at 30° C. for 1 hour. Glycyl-3-cyclohexyl-D-alanine (12.5 mg, 0.055 mmol) was added and the reaction mixture was stirred for 2 hours. The reaction mixture was purified with preparative HPLC on a C8 column. A gradient from 10 to 100% MeCN in 0.1M NH$_4$OAc buffer was used as eluent. Most of the MeCN was removed under reduced pressure. The residue was diluted with water and lyophilised to give the title compound, M/z: 921 (M−1).

Method 2

N-({4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetyl)glycyl-N$^6$-(tert-butoxycarbonyl)-D-lysine {4-[(2R,3R)-3-{[(2R)-2-{[tert-butyl(dimethyl)silyl]oxy}-2-(4-fluorophenyl)ethyl]thio}-(4-{3-[(methylsulfonyl)amino]prop-1-yn-1-yl}phenyl)-4-oxoazetidin-2-yl]phenoxy}acetic acid (Method 8) (15.1 mg, 0.021 mmol) was dissolved in DMF (1 ml, dry). N-methylmorpholine (7 μl, 0.064 mmol) was added and the reaction mixture was stirred at 30° C. for five minutes. TBTU (10.8 mg, 0.034 mmol) was added and the reaction mixture was stirred at the same conditions for 1 hour. Glycyl-N$^6$-(tert-butoxycarbonyl)-D-lysine (10.0 mg 0.033 mmol) was added and the reaction mixture was stirred for 2 hours. The mixture was purified with preparative HPLC on a C8 column. A gradient from 10 to 100% MeCN in a 0.1M NH$_4$OAc buffer was used as eluent. The pure fractions were collected and most of the MeCN was removed under reduced pressure. The residue was lyophilised to give the title compound. M/z: 996.74 (M−1).

Method 3

N-({4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetyl)glycine {4-[(2R,3R)-3-{[(2R)-2-{[tert-butyl(dimethyl)silyl]oxy}-2-(4-fluorophenyl)ethyl]thio}-(4-{3-[(methylsulfonyl)amino]prop-1-yn-1-yl}phenyl)-4-oxoazetidin-2-yl]phenoxy}acetic acid (19.0 mg, 0.020 mmol) was dissolved in DCM (2 ml). Methyl glycinate hydrochloride (4.1 mg, 0.033 mmol) and N-methylmorpholine (6 μl, 0.059 mmol) were added and the reaction mixture was stirred for five minutes. TBTU (9.5 mg, 0.029 mmol) was added and the reaction mixture was stirred for 2 hours. The solvent was removed under reduced pressure. The formation of the methylester of the titled compound was confirmed, M/z: 782.55 (M−1). The residue was suspended in MeCN (1 ml). Triethylamine (27 μl, 0.19 mmol), water (7 μl) and LiCl (24.8 mg, 0.66 mmol) were added and the reaction mixture was stirred at 35° C. overnight. Additional triethylamine (15 μl, 0.11 mmol) and water (15 μl) were added and the reaction mixture was stirred at 35° C. for 5 hours. MeCN (1 ml) was added and the mixture was stirred overnight. The reaction mixture was purified with preparative HPLC on a C8 column. A gradient from 20 to 85% MeCN in 0.1M NH$_4$OAc buffer was used as eluent. Most of the MeCN was removed under reduced pressure and the residue was acidified to pH 3 with KHSO$_4$, (2M) and extracted from DCM. The phases were separated and the organic phase was passed through a phase separator. The solvent was removed under reduced pressure. The residue was diluted with water and MeCN and lyophilised to give the title compound. H-NMR (400 MHz, DMSO-d$_6$) 0.00 (s, 3H), 0.14 (s, 3H), 0.95 (s, 9H), 3.03-3.14 (m 2H), 3.16 (s, 3H), 3.97 (d, 2H), 4.19 (d, 2H), 4.48 (d, 2H), 4.70 (s, 2H), 5.10 (t, 1H), 5.30 8d, 1H), 7.18 (2H), 7.32 (t, 2H), 7.40 (d, 2H), 7.52-7.59 (m, 6H), 7.76 (t, 1H), 8.52 (t, 1H). M/z: 768.60 (M−1).

Method 4

Glycyl-3-cyclohexyl-D-alanine

N-(tert-butoxycarbonyl)glycine (2.0 g, 11.4 mmol) and DIPEA (4.0 g, 31 mmol) were dissolved in methylene chloride (25 ml). TBTU (4.1 g, 12.8 mmol) was added and the mixture was stirred for 15 min at room temperature. 3-cyclohexyl-D-alanine (2.1 g, 12.2 mmol) was added and the reaction mixture was stirred over night at room temperature. The reaction mixture was transferred to a separation funnel and was then extracted with a water/acetic acid solution (100 ml 5% acetic acid). The organic layer was separated and evaporated under reduced pressure. The residue was dissolved in formic acid (20 ml) and the mixture was stirred over night at 40° C. The formic acid was removed under reduced pressure. The residue was washed with water (50 ml) and then stirred in acetone (25 ml) for 1 h at room temperature. The solid material was filtered off and washed with acetone (20 ml). The title compound was obtained.

$^1$H-NMR, 300 MHz, CD3COOD): 0.8-1.9 (m, 13H), 3.9-4.1 (m, 2H), 4.55-4.65 (m, 1H).

Method 5

Methyl (4-{(E)-[(4-iodophenyl)imino]methyl}phenoxy)acetate

Methyl (4-formylphenoxy)acetate (8.0 g, 40 mmol) was dissolved in 100 ml toluene and p-iodoaniline (9.1 g, 40 mmol) was added. The mixture was refluxed over night using a Dean-Stark apparatus. The reaction mixture was partly evaporated under reduced pressure. Methanol was added to the suspension and the mixture was stirred for a few minutes. The precipitate was filtered off, washed with methanol and dried under reduced pressure over night to yield the title compound. $^1$H-NMR (400 MHz, CDCl$_3$) δ: 3.83 (s, 3H), 4.72 (s, 2H), 6.95 (d, 2H), 7.00 (d, 2H), 7.69 (d, 2H), 7.86 (d, 2H), 8.35 (s, 1H).

Method 6

Methyl {4-[(2R,3R)-3-{[(2R)-2-{[tert-butyl(dimethyl)silyl]oxy}-2-(4-fluorophenyl)ethyl]thio}-1-(4-iodophenyl)-4-oxoazetidin-2-yl]phenoxy}acetate Methyl (4-{(E)-[(4-iodophenyl)imino]methyl}phenoxy)acetate (7.0 g, 17.7 mmol), was placed in a dry 250 ml 3-necked flask under inert atmosphere and dissolved in 100 ml dry DCM. $Et_3N$ (5.5 ml, 39.5 mmol) and 2-chloro-1-methylpyridinium iodide (4.2 g, 16.4 mmol) were added. {[(2R)-2-{[tert-Butyl(dimethyl)silyl]oxy}-2-(4-fluorophenyl)ethyl]thio}acetic acid (5.4 g, 15.7 mmol) was dissolved in 50 ml dry DCM and slowly added to the above solution over 7-8 h. The mixture was stirred over night and diluted with 50 ml DCM. HCl (1 M, 100 ml) was added followed by $NaHCO_3$ (5%) until pH was 8-9 of the aqueous. The organic phase was washed with 0.3 M $KHSO_4$, brine until neutral pH, dried with $MgSO_4$ and concentrated. The solid was dissolved in EtOAc:heptane (4:1) and filtered on a short $SiO_2$ column using a gradient from ¼ to ½ of EtOAc/heptane as eluent. Concentration yielded 10.65 g. The mixture was purified by preparative HPLC on a C8 column (500×50 mm) using a gradient from 20-100% MeCN in 0.1 M ammonium acetate as eluent. The product fraction was concentrated to yield 7.13 g of the trans diastereomeric mixture. M/z: 720.2 (M−1). The diastereomeric mixture was separated by HPLC on a Chiralpak IA column (4.6×250 mm) using heptane/THF (80/20) as mobile phase. The second eluting diastereomer was collected and the solution concentrated to yield the title compound. $^1$H-NMR (400 MHz, MeOD) δ: −0.13 (s, 3H), 0.02 (s, 3H), 0.85 (s, 9H), 3.00 (ddd, 2H), 3.81 (s, 3H), 4.02 (d, 1H), 4.76 (s, 2H), 4.84-4.90 (m, 1H), 4.94 (dd, 1H), 6.97-7.06 (m, 4H), 7.09 (d, 2H), 7.30-7.40 (m, 4H), 7.61 (d, 2H).

Method 7

Methyl {4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetate Methyl {4-[(2R,3R)-3-{[(2R)-2-{[tert-butyl(dimethyl)silyl]oxy}-2-(4-fluorophenyl)ethyl]thio}-1-(4-iodophenyl)-4-oxoazetidin-2-yl]phenoxy}acetate (500 mg, 0.69 mmol) and N-prop-2-yn-1-ylmethanesulfonamide (150 mg, 1.13 mmol) were mixed in 15 ml water and 4 ml MeCN. $K_2CO_3$ (220 mg, 1.59 mmol), $Pd(PPh_3)_4$ (40 mg, 5 mol %) and CuI (13 mg, 10 mol %) were added. The solution was stirred at 50° C. for 2 h and at ambient temperature over night. EtOAc (20 ml) and 2 M HCl (1 ml) were added. The mixture was stirred for 5 min and the phases were separated. The aqueous phase was extracted with EtOAc. The combined organic phases were washed with 2% $NaHCO_3$, brine (2×), dried with $MgSO_4$ and concentrated to yield the title compound. M/z: 725.3 (M−1). $^1$H-NMR (400 MHz, DMSO-$d_6$) δ: −0.18 (s, 3H), −0.04 (s, 3H), 0.77 (s, 9H), 2.85-3.02 (m, 5H), 3.69 (s, 3H), 3.80 (dd, 1H), 4.01 (d, 2H), 4.29 (d, 1H), 4.79 (s, 2H), 4.91 (dd, 1H), 5.11 (d, 1H), 6.95 (d, 2H), 7.09-7.18 (m, 2H), 7.18-7.25 (d, 2H), 7.32-7.42 (m, 6H).

Method 8

{4-[(2R,3R)-3-{[(2R)-2-[[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetic acid Methyl {4-[(2R,3R)-3-{[(2R)-2-{[tert-butyl(dimethyl)silyl]oxy}-2-(4-fluorophenyl)ethyl]thio}-1-(4-{3-[(methylsulfonyl)amino]prop-1-yn-1-yl}phenyl)-4-oxoazetidin-2-yl]phenoxy}acetate (530 mg, 0.73 mmol) was dissolved in 15 ml MeCN. Water (0.2 ml), $Et_3N$ (1.0 ml, 7.2 mmol) and LiCl (630 mg, 14.9 mmol) were added and the mixture was stirred at 35° C. over night. The mixture was filtered and concentrated. The residue was extracted between EtOAc and 0.3 M $KHSO_4$. The aqueous phase was extracted with EtOAc and the combined organic phases were washed with brine (2×) and concentrated. The brown residue was purified by preparative HPLC on a C8 column (150×30 mm) using a gradient from 20-60% MeCN in 0.1 M ammonium acetate as eluent. The title compound was obtained in 170 mg (33%) as a slightly brownish solid. M/z: 711.2 (M−1). $^1$H-NMR (400 MHz, DMSO-$d_6$) δ: −0.18 (s, 3H), −0.04 (s, 3H), 0.78 (s, 9H), 2.93 (ddd, 2H), 2.98 (s, 3H), 4.01 (d, 2H), 4.29 (d, 1H), 4.67 (s, 2H), 4.88-4.94 (m, 1H), 5.11 (d, 1H), 6.93 (d, 2H), 7.09-7.18 (m, 2H), 7.21 (d, 2H), 7.32-7.42 (m, 6H), 7.58 (t, 1H), 12.97 (brs, 1H).

Method 9

Glycyl-3-methyl-D-valine trifluoroacetate

To a 30° C. solution of N-(tert-butoxycarbonyl)glycine (0.450 g, 2.569 mmol) and N-methylmorpholine (1.30 g, 12.84 mmol) in $CH_2Cl_2$ (50 ml) was added TBTU (0.99 g, 3.08 mmol). After 1.5 h, D-tert-leucine (0.303 g, 2.31 mmol) was added. After 30 minutes, the reaction was quenched by the addition of water (1 ml). The mixture was concentrated and the residue was purified through preparative HPLC using an eluent of 0-40% $CH_3CN$ in 0.1M $NH_4OAc$ buffer. Pure fractions were collected and concentrated. To the residue were added $CH_2Cl_2$ (10 ml) and TFA (3 ml). Full conversion to the corresponding aminoacid was obtained after 30 minutes. The reaction mixture was concentrated to give the desired compound. $^1$H NMR [$(CD_3)_2SO$), 400 MHz] δ:0.94 (s, 9H), 3.60-3.67 (m, 2H), 4.16 (d, 1H), 7.90-8.00 (m, 3H), 8.47 (d, 1H).

It will be appreciated by those skilled in the art that the examples may be modified within the realms of the invention, why the invention is not limited to particular embodiments.

Absorption

Absorption of the compounds of formula (I) was tested in a Caco-2 cells model (Gastroenterology 1989, 96, 736):

| Compound (I) | Caco value ($10^{-6}$ cm/sec) |
|---|---|
| N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-D-valine | 0.02 |
| N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-3-cyclohexyl-D-alanine | 0.04 |

The invention claimed is:

1. A compound of formula (I):

(I)

wherein:
- $R^1$ is hydrogen, $C_{1-6}$alkyl, $C_{3-6}$cycloalkyl or aryl;
- $R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, $(C_1$-$C_4$ alkyl$)_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl, $C_{1-6}$alkoxy, and cyano;
- $R^3$ is hydrogen, alkyl, halo, $C_{1-6}$alkoxy or $C_{1-6}$ alkylS-;
- $R^4$ is methyl or aryl;
- $R^6$ is hydrogen, $C_{1-6}$ alkyl, or aryl$C_{1-6}$ alkyl;

wherein $R^5$ and $R^2$ may form a ring with 2-7 carbon atoms and wherein $R^6$ and $R^2$ may form a ring with 3-6 carbon atoms;

n=0 or 1;

or a pharmaceutically acceptable salt or a prodrug thereof.

2. A compound of formula (I2):

(I2)

wherein:
- $R^1$ is hydrogen, $C_{1-6}$alkyl, $C_{3-6}$cycloalkyl or aryl;
- $R^2$ and $R^5$ are independently hydrogen, a branched or unbranched $C_{1-6}$alkyl, hydroxy, amino, guanidino, cyano, carbamoyl, carboxy, $C_{1-6}$alkoxy, aryl $C_{1-6}$alkoxy, $(C_1$-$C_4$ alkyl$)_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl, $C_{1-6}$alkoxy, and cyano;
- $R^3$ is hydrogen, alkyl, halo, $C_{1-6}$alkoxy or $C_{1-6}$ alkylS-;
- $R^4$ is methyl or aryl;
- $R^6$ is hydrogen, $C_{1-6}$ alkyl, or aryl$C_{1-6}$ alkyl;

wherein $R^5$ and $R^2$ may form a ring with 2-7 carbon atoms and wherein $R^6$ and $R^2$ may form a ring with 3-6 carbon atoms;

n=0 or 1 or a pharmaceutically acceptable salt or a prodrug thereof.

3. A compound according to claim 1, wherein: $R^1$ is hydrogen.

4. A compound according to claim 1, wherein: $R^2$ and $R^5$ are, independently, hydrogen or a branched or unbranched $C_{1-6}$alkyl, $C_{3-6}$cycloalkyl or aryl; wherein said $C_{1-6}$alkyl may be optionally substituted by one or more hydroxyl or amino.

5. A compound according to claim 1, wherein: $R^3$ is halo.

6. A compound according to claim 1, wherein: $R^3$ is fluorine.

7. A compound according to claim 1, wherein: $R^6$ is hydrogen.

8. A compound according to claim 1 wherein:
- $R^1$ hydrogen;
- $R^2$ and $R^5$ are hydrogen or a branched or unbranched $C_{1-6}$alkyl, $C_{3-6}$cycloalkyl or aryl;

wherein said $C_{1-6}$alkyl may be optionally substituted by one or more hydroxyl or amino;
- $R^3$ is halo; and
- $R^6$ is hydrogen.

9. One or more compounds chosen from:
- N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-3-cyclohexyl-D-alanine;
- N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-D-valine;
- N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-3-methyl-D-valine;
- N-({4-[(2R,3R)-3-{[(2R)-2-(4-fluorophenyl)-2-hydroxyethyl]thio}-1-(4-{3-[(methylsulfonyl)amino]prop-1-yn-1-yl}phenyl)-4-oxoazetidin-2-yl]phenoxy}acetyl)glycyl-D-lysine;

N-({4-[(2R,3R)-3-{[(2R)-2-(4-fluorophenyl)-2-hydroxy-ethyl]thio}-1-(4-{3-[(methylsulfonyl)amino]prop-1-yn-1-yl}phenyl)-4-oxoazetidin-2-yl]phenoxy}acetyl) glycylglycine; and N-({4-[(2R,3R)-3-{[(2R)-2-(4-fluorophenyl)-2-hydroxy-ethyl]thio}-1-(4-{3-[(methylsulfonyl)amino]prop-1-yn-1-yl}phenyl)-4-oxoazetidin-2-yl]phenoxy}acetyl) glycine.

10. A pharmaceutical formulation comprising a compound according to claim 1 in admixture with a pharmaceutically acceptable adjuvant, diluent and/or carrier.

11. A combination of a compound according to formula (I) or (I2)

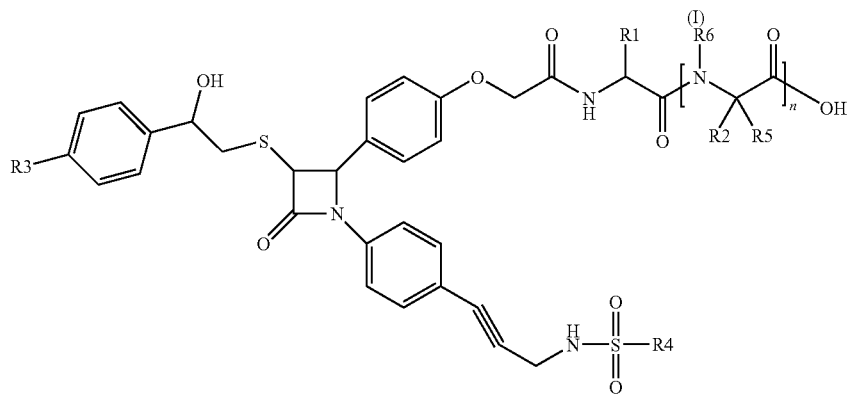

wherein:
$R^1$ is hydrogen, $C_{1-6}$alkyl, $C_{3-6}$cycloalkyl or aryl;
$R^2$ and $R^5$ are independently hydrogen, a branched or unbranched $C_{1-6}$alkyl, $C_{3-6}$cycloalkyl or aryl; wherein said $C_{1-6}$alkyl may be optionally substituted by one or more hydroxy, amino, guanidino, cyano, carbamoyl, carboxy, $C_{1-6}$alkoxy, aryl $C_{1-6}$alkoxy, $(C_1-C_4$ alkyl$)_3$Si, N-($C_{1-6}$alkyl)amino, N,N-($C_{1-6}$alkyl)$_2$amino, $C_{1-6}$alkylS(O)$_a$, $C_{3-6}$cycloalkyl, aryl or aryl $C_{1-6}$ alkylS(O)$_a$, wherein a is 0-2; and wherein any aryl group may be optionally substituted by one or two substituents selected from halo, hydroxy, $C_{1-6}$alkyl, $C_{1-6}$alkoxy, and cyano;
$R^3$ is hydrogen, alkyl, halo, $C_{1-6}$alkoxy or $C_{1-6}$ alkylS-;
$R^4$ is methyl or aryl;
$R^6$ is hydrogen, $C_{1-6}$ alkyl, or aryl$C_{1-6}$ alkyl;
wherein $R^5$ and $R^2$ may form a ring with 2-7 carbon atoms and wherein $R^6$ and $R^2$ may form a ring with 3-6 carbon atoms;
n=0 or 1;
or a pharmaceutically acceptable salt or a prodrug thereof

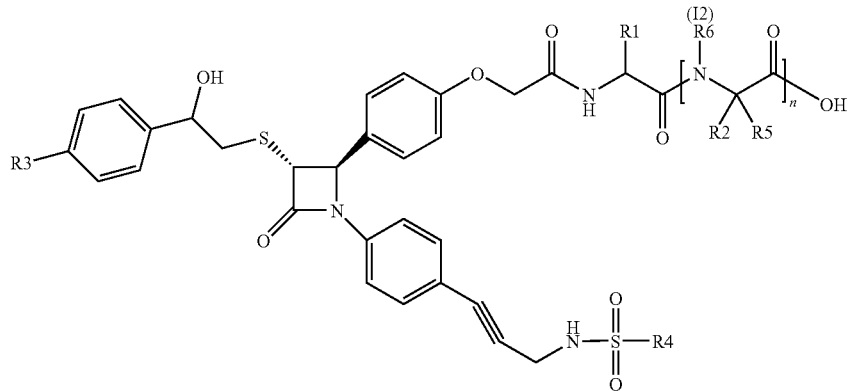

wherein:
R$^1$ is hydrogen, C$_{1-6}$alkyl, C$_{3-6}$cycloalkyl or aryl;
R$^2$ and R$^5$ are independently hydrogen, a branched or unbranched C$_{1-6}$alkyl, hydroxy, amino, guanidino, cyano, carbamoyl, carboxy, C$_{1-6}$alkoxy, arylC$_{1-6}$alkoxy, (C$_1$-C$_4$ alkyl)$_3$Si, N-(C$_{1-6}$alkyl)amino, N,N-(C$_{1-6}$alkyl)$_2$amino, C$_{1-6}$alkylS(O)$_a$, C$_{3-6}$cycloalkyl, aryl or aryl C$_{1-6}$alkylS(O)$_a$, wherein a is 0-2; and wherein any aryl group may be optionally substituted by one or two substituents selected from halo, hydroxy, C$_{1-6}$alkyl, C$_{1-6}$alkoxy, and cyano;
R$^3$ is hydrogen, alkyl, halo, C$_{1-6}$alkoxy or C$_{1-6}$ alkylS-;
R$^4$ is methyl or aryl;
R$^6$ is hydrogen, C$_{1-6}$ alkyl, or arylC$_{1-6}$ alkyl;
wherein R$^5$ and R$^2$ may form a ring with 2-7 carbon atoms and wherein R$^6$ and R$^2$ may form a ring with 3-6 carbon atoms;
n=0 or 1;
or a pharmaceutically acceptable salt or a prodrug thereof with a PPAR alpha and/or gamma agonist.

12. A combination of a compound according to formula (I) or (I2)

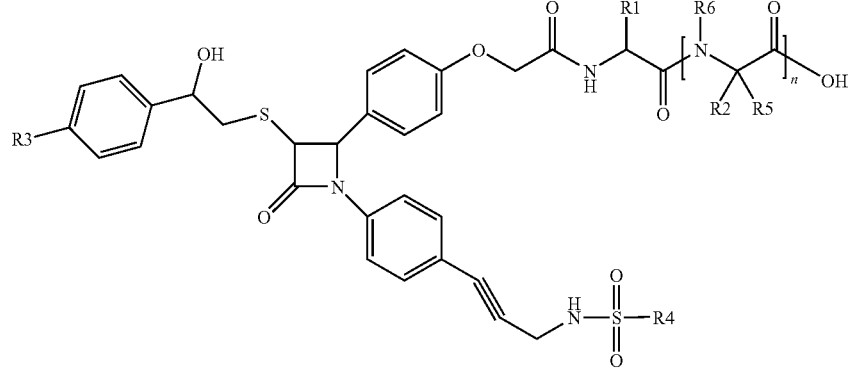

(I)

wherein:
R$^1$ is hydrogen, C$_{1-6}$alkyl, C$_{3-6}$cycloalkyl or aryl;
R$^2$ and R$^5$ are independently hydrogen, a branched or unbranched C$_{1-6}$alkyl, C$_{3-6}$cycloalkyl or aryl; wherein said C$_{1-6}$alkyl may be optionally substituted by one or more hydroxy, amino, guanidino, cyano, carbamoyl, carboxy, C$_{1-6}$alkoxy, aryl C$_{1-6}$alkoxy, (C$_1$-C$_4$ alkyl)$_3$Si, N-(C$_{1-6}$alkyl)amino, N,N-(C$_{1-6}$alkyl)$_2$amino, C$_{1-6}$alkylS(O)$_a$, C$_{3-6}$cycloalkyl, aryl or aryl C$_{1-6}$ alkylS(O)$_a$, wherein a is 0-2; and wherein any aryl group may be optionally substituted by one or two substituents selected from halo, hydroxy, C$_{1-6}$alkyl, C$_{1-6}$alkoxy, and cyano;
R$^3$ is hydrogen, alkyl, halo, C$_{1-6}$alkoxy or C$_{1-6}$ alkylS-;
R$^4$ is methyl or aryl;
R$^6$ is hydrogen, C$_{1-6}$ alkyl, or arylC$_{1-6}$ alkyl;
wherein R$^5$ and R$^2$ may form a ring with 2-7 carbon atoms and wherein R$^6$ and R$^2$ may form a ring with 3-6 carbon atoms;
n=0 or 1;
or a pharmaceutically acceptable salt or a prodrug thereof

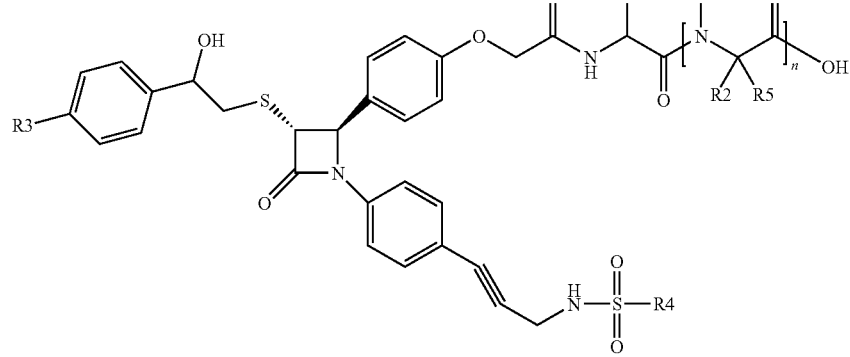

(I2)

wherein:

$R^1$ is hydrogen, $C_{1-6}$alkyl, $C_{3-6}$cycloalkyl or aryl;

$R^2$ and $R^5$ are independently hydrogen, a branched or unbranched $C_{1-6}$alkyl, hydroxy, amino, guanidino, cyano, carbamoyl, carboxy, $C_{1-6}$alkoxy, aryl$C_{1-6}$alkoxy, $(C_1$-$C_4$ alkyl$)_3$Si, N-($C_{1-6}$alkyl)amino, N,N-($C_{1-6}$alkyl$)_2$amino, $C_{1-6}$alkylS(O)$_a$, $C_{3-6}$cycloalkyl, aryl or aryl$C_{1-6}$alkylS(O)$_a$, wherein a is 0-2; and wherein any aryl group may be optionally substituted by one or two substituents selected from halo, hydroxy, $C_{1-6}$alkyl, $C_{1-6}$alkoxy, and cyano;

$R^3$ is hydrogen, alkyl, halo, $C_{1-6}$alkoxy or $C_{1-6}$ alkylS-;

$R^4$ is methyl or aryl;

$R^6$ is hydrogen, $C_{1-6}$ alkyl, or aryl$C_{1-6}$ alkyl;

wherein $R^5$ and $R^2$ may form a ring with 2-7 carbon atoms and wherein $R^6$ and $R^2$ may form a ring with 3-6 carbon atoms;

n=0 or 1;

or a pharmaceutically acceptable salt or a prodrug thereof with an HMG Co-A reductase inhibitor.

* * * * *